US012558167B2

(12) United States Patent
Braido et al.

(10) Patent No.: US 12,558,167 B2
(45) Date of Patent: Feb. 24, 2026

(54) EXTENDED INTELLIGENCE FOR CARDIAC IMPLANTABLE ELECTRONIC DEVICE (CIED) PLACEMENT PROCEDURES

(71) Applicant: Medtronic, Inc., Minneapolis, MN (US)

(72) Inventors: Peter N. Braido, Linwood, MN (US); Randal C. Schulhauser, Phoenix, AZ (US); Xiaohong Zhou, Woodbury, MN (US); Alan Cheng, Golden Valley, MN (US); Zhongping Yang, Woodbury, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 431 days.

(21) Appl. No.: 17/700,622

(22) Filed: Mar. 22, 2022

(65) Prior Publication Data

US 2022/0361954 A1      Nov. 17, 2022

Related U.S. Application Data

(60) Provisional application No. 63/187,738, filed on May 12, 2021.

(51) Int. Cl.
*A61B 34/20* (2016.01)
*A61N 1/362* (2006.01)
(Continued)

(52) U.S. Cl.
CPC .............. *A61B 34/20* (2016.02); *A61N 1/362* (2013.01); *G16H 20/40* (2018.01); *G16H 30/40* (2018.01);
(Continued)

(58) Field of Classification Search
CPC .............. A61B 34/20; A61B 2034/303; A61B 2090/365; A61B 5/021; A61B 5/024;
(Continued)

(56) References Cited

U.S. PATENT DOCUMENTS 7,187,964 B2    3/2007  Khoury
7,892,165 B2    2/2011  Nakamura
(Continued)

FOREIGN PATENT DOCUMENTS

JP       2019109739 A    7/2019
WO        0120552 A1     3/2001
(Continued)

OTHER PUBLICATIONS

Goo, Hyun Woo, Sang Joon Park, and Shi-Joon Yoo. "Advanced medical use of three-dimensional imaging in congenital heart disease: augmented reality, mixed reality, virtual reality, and three-dimensional printing." Korean journal of radiology 21.2 (2020): 133-145. (Year: 2020).*
(Continued)

*Primary Examiner* — Yu Chen
(74) *Attorney, Agent, or Firm* — Weaver Austin Villeneuve & Sampson LLP

(57) ABSTRACT

Novel tools and techniques are provided for implementing intelligent assistance ("IA") or extended intelligence ("EI") ecosystem to placement procedures for cardiac implantable electronic device ("CIED"). In various embodiments, a computing system might analyze received one or more first layer input data (i.e., room content-based data) and received one or more second layer input data (i.e., patient and/or tool-based data), and might generate one or more recommendations for guiding a medical professional in performing a CIED placement procedure in a heart of the patient, based at least in part on the analysis, the generated one or more
(Continued)

recommendations comprising 3D or 4D mapped guides toward, in, and around the heart of the patient. The computing system might then generate one or more XR images, based at least in part on the generated one or more recommendations, and might present the generated one or more XR images using a UX device.

19 Claims, 14 Drawing Sheets

(51) Int. Cl.

| | |
|---|---|
| *G16H 20/40* | (2018.01) |
| *G16H 30/40* | (2018.01) |
| *G16H 50/20* | (2018.01) |
| *A61B 34/30* | (2016.01) |
| *A61B 90/00* | (2016.01) |
| *A61N 1/39* | (2006.01) |

(52) U.S. Cl.
CPC ........ *G16H 50/20* (2018.01); *A61B 2034/303* (2016.02); *A61B 2090/365* (2016.02); *A61N 1/3956* (2013.01)

(58) Field of Classification Search
CPC ....... A61B 5/053; A61B 5/055; A61B 5/1116; A61B 5/14546; A61B 5/369; A61B 5/389; A61B 5/398; A61B 5/4806; A61B 5/4824; A61B 5/6852; A61B 5/745; A61B 2017/00243; A61B 5/0205; A61B 5/1113; A61B 5/6889; A61B 34/10; A61B 2034/107; A61B 2034/2048; A61B 2034/2051; A61B 2034/252; A61B 34/30; A61B 2505/05; A61B 90/36; A61B 5/0044; A61N 1/362; A61N 1/3956; A61N 1/3756; A61N 1/372; G16H 20/40; G16H 30/40; G16H 50/20
See application file for complete search history.

(56) References Cited

U.S. PATENT DOCUMENTS

| | | | |
|---|---|---|---|
| 7,998,095 | B2 | 8/2011 | McAuley |
| 8,460,282 | B2 | 6/2013 | McAuley |
| 8,482,859 | B2 | 7/2013 | Border et al. |
| 8,768,022 | B2 | 7/2014 | Miga et al. |
| 8,792,693 | B2 | 7/2014 | Satish et al. |
| 8,902,254 | B1 | 12/2014 | Laughlin et al. |
| 9,128,281 | B2 | 9/2015 | Osterhout et al. |
| 9,134,534 | B2 | 9/2015 | Border et al. |
| 9,223,134 | B2 | 12/2015 | Miller et al. |
| 9,232,982 | B2 | 1/2016 | Soler et al. |
| 9,298,884 | B1 | 3/2016 | Ahmad |
| 9,317,743 | B2 | 4/2016 | Datta et al. |
| 9,452,294 | B2 | 9/2016 | Kaula et al. |
| 9,492,241 | B2 | 11/2016 | Joskowicz et al. |
| 9,526,443 | B1 | 12/2016 | Berme et al. |
| 9,615,788 | B2 | 4/2017 | Kaula et al. |
| 9,639,953 | B2 | 5/2017 | Moraviec |
| 9,642,606 | B2 | 5/2017 | Charles et al. |
| 9,659,104 | B2 | 5/2017 | Soon-Shiong et al. |
| 9,687,301 | B2 | 6/2017 | Lee et al. |
| 9,720,505 | B2 | 8/2017 | Gribetz et al. |
| 9,740,296 | B2 | 8/2017 | Cohen et al. |
| 9,767,608 | B2 | 9/2017 | Lee et al. |
| 9,773,312 | B2 | 9/2017 | Lee |
| 9,855,103 | B2 | 1/2018 | Tsekos et al. |
| 9,866,767 | B2 | 1/2018 | Jones |
| 9,870,060 | B2 | 1/2018 | Marggraff et al. |
| 9,875,540 | B2 | 1/2018 | Blumhofer et al. |
| 9,888,973 | B2 | 2/2018 | Olson et al. |
| 9,911,225 | B2 | 3/2018 | Engel et al. |
| 9,928,588 | B2 | 3/2018 | Vilsmeier |
| 9,947,104 | B2 | 4/2018 | Seiler et al. |
| 9,986,983 | B2 | 6/2018 | Weingarten et al. |
| 10,026,227 | B2 | 7/2018 | Laughlin et al. |
| 10,152,796 | B2 | 12/2018 | Guo et al. |
| 10,180,572 | B2 | 1/2019 | Osterhout et al. |
| 10,665,337 | B2 | 5/2020 | Schulhauser et al. |
| 11,005,661 | B1 | 5/2021 | Neumann |
| 11,037,679 | B1 | 6/2021 | Neumann |
| 11,207,133 | B1 | 12/2021 | Douglas et al. |
| 11,217,033 | B1 | 1/2022 | Morgan et al. |
| 11,270,789 | B1 | 3/2022 | Neumann |
| 12,070,362 | B2 | 8/2024 | Braido et al. |
| 12,193,888 | B2 | 1/2025 | Braido et al. |
| 12,220,176 | B2 | 2/2025 | Calloway et al. |
| 2002/0198891 | A1 | 12/2002 | Li et al. |
| 2007/0173861 | A1 | 7/2007 | Strommer et al. |
| 2008/0033527 | A1 | 2/2008 | Nunez et al. |
| 2010/0198346 | A1 | 8/2010 | Keogh et al. |
| 2012/0188352 | A1 | 7/2012 | Wittenberg et al. |
| 2013/0035757 | A1 | 2/2013 | Zentgraf et al. |
| 2014/0128726 | A1 | 5/2014 | Quill et al. |
| 2014/0176661 | A1 | 6/2014 | Smurro et al. |
| 2014/0296704 | A1 | 10/2014 | Alves et al. |
| 2015/0037201 | A1* | 2/2015 | Armour ................... A61L 2/10 |
| | | | 600/203 |
| 2016/0019716 | A1 | 1/2016 | Huang et al. |
| 2016/0085774 | A1 | 3/2016 | Bhamidipati et al. |
| 2016/0157798 | A1 | 6/2016 | Anderson |
| 2016/0350303 | A1 | 12/2016 | Fischer et al. |
| 2017/0021132 | A1 | 1/2017 | Laby et al. |
| 2017/0098333 | A1 | 4/2017 | Varga |
| 2017/0103581 | A1 | 4/2017 | Mullins et al. |
| 2017/0109484 | A1 | 4/2017 | Herger et al. |
| 2017/0206419 | A1 | 7/2017 | Mullins |
| 2017/0221387 | A1 | 8/2017 | Lampotang et al. |
| 2017/0258526 | A1 | 9/2017 | Lang |
| 2017/0258586 | A1 | 9/2017 | Bateman et al. |
| 2017/0293805 | A1 | 10/2017 | Kontschieder et al. |
| 2017/0323148 | A1 | 11/2017 | Sarkar et al. |
| 2017/0340396 | A1 | 11/2017 | Romo et al. |
| 2017/0367771 | A1 | 12/2017 | Tako et al. |
| 2018/0012416 | A1 | 1/2018 | Jones et al. |
| 2018/0140328 | A1 | 5/2018 | Shuros et al. |
| 2018/0350010 | A1 | 12/2018 | Kuper et al. |
| 2019/0183576 | A1 | 6/2019 | Fahim et al. |
| 2019/0183577 | A1 | 6/2019 | Fahim et al. |
| 2019/0262617 | A1 | 8/2019 | Ghosh |
| 2019/0298450 | A1 | 10/2019 | Dasi et al. |
| 2019/0307516 | A1 | 10/2019 | Schotzko et al. |
| 2019/0350671 | A1 | 11/2019 | Varshney et al. |
| 2019/0362556 | A1 | 11/2019 | Ben-Dor et al. |
| 2019/0384764 | A1 | 12/2019 | Taylor |
| 2020/0060765 | A1* | 2/2020 | Fahim ................ A61B 17/3478 |
| 2020/0121898 | A1 | 4/2020 | Christopher et al. |
| 2020/0129136 | A1 | 4/2020 | Harding et al. |
| 2020/0138518 | A1 | 5/2020 | Lang |
| 2020/0151874 | A1 | 5/2020 | Peterson et al. |
| 2020/0321123 | A1 | 10/2020 | Neumann |
| 2020/0323516 | A1 | 10/2020 | El Kaffas et al. |
| 2020/0391016 | A1 | 12/2020 | Passman et al. |
| 2021/0052348 | A1 | 2/2021 | Schwägli et al. |
| 2021/0137634 | A1* | 5/2021 | Lang ...................... A61B 90/98 |
| 2021/0192759 | A1 | 6/2021 | Lang |
| 2021/0287783 | A1 | 9/2021 | Jhaveri |
| 2021/0369393 | A1 | 12/2021 | Braido et al. |
| 2021/0369394 | A1 | 12/2021 | Braido et al. |
| 2022/0029986 | A1 | 1/2022 | Neumann |
| 2022/0167929 | A1 | 6/2022 | Neumann |
| 2023/0008264 | A1 | 1/2023 | Mangual-Soto et al. |
| 2023/0057317 | A1 | 2/2023 | Kadidal et al. |
| 2023/0143522 | A1 | 5/2023 | Keast |
| 2023/0157757 | A1 | 5/2023 | Braido et al. |
| 2023/0157762 | A1 | 5/2023 | Braido et al. |
| 2023/0230321 | A1* | 7/2023 | Schreckenberg ..... G06F 3/0346 |
| | | | 345/419 |

(56) References Cited

U.S. PATENT DOCUMENTS

2023/0309832 A1 10/2023 Braido et al.
2023/0317248 A1 10/2023 Braido et al.

FOREIGN PATENT DOCUMENTS

WO      2009148317 A1    12/2009
WO      2021243310 A1    12/2021
WO      2021243311 A1    12/2021
WO      2021243313 A1    12/2021
WO      2021243314 A1    12/2021

OTHER PUBLICATIONS

Gu, M. et al., "Permanent His Bundle Pacing Implantation Facilitated by Visualization of the Tricuspid Valve Annulus," Circ Arrhythm Electrophysiol. (2020), doi: 10.1161/CIRCEP.120.008370, 11 pages.
Lin, J. et al., "Bilateral Bundle Branch Area Pacing to Achieve Physiological Conduction System Activation," Circ Arrhythm Electrophysiol. (2020), doi: 10.1161/CIRCEP.119.008267, 11 pages.
Liu, X. et al., "Contrast-enhanced image guided lead deployment for left bundle branch pacing," Heart Rhythm (2021), doi: https://doi.org/10.1016/j.hrthm.2021.04.015, 8 pages.
Azizian, M., et al., "Intraoperative 3d Stereo Visualization for Image-guided Cardiac Ablation", Medical Imaging 2011: Visualization, Image-guided Procedures, and Modeling, SPIE, Mar. 2, 2011, vol. 7964, No. 1, 8 pages.
Doughty, M., et al., "Surgeonassist-net: Towards Contextaware Head-mounted Display-based Augmented Reality for Surgical Guidance", 16th European Conference—Computer Vision—ECCV 2020, pp. 667-677.
Gloud M.K., et al., "Evaluation of Individuals With Pulmonary Nodules: When Is It Lung Cancer?," Diagnosis and Management of Lung Cancer, 3rd Ed: Accp Guidelines, Chest, 2013, vol. 143 (5 Suppl), pp. 1-28.
International Preliminary Report on Patentability dated Dec. 8, 2022, in PCT Application No. PCT/US2021/035037.
International Preliminary Report on Patentability dated Dec. 8, 2022, in PCT Application PCT/US2021/035036.
International Search Report Written Opinion dated Sep. 14, 2021, in Application No. PCT/US2021/035033.
International Search Report Written Opinion dated Sep. 16, 2021, in Application No. PCT/US2021/035034.
International Search Report and Written Opinion dated in Application No. Sep. 16, 2021 PCT/US2021/035037.
International Search Report and Written Opinion dated Jan. 27, 2023 in PCT Application No. PCT/IB2022/060244.
International Search Report and Written Opinion dated Oct. 4, 2021, in Application No. PCT/US2021/037655.
International Search Report and Written Opinion dated Sep. 16, 2021 in Application No. PCT/US2021/035036.
Li C., et al., "Augmented Reality Navigation-guided Pulmonary Nodule Localization in a Canine Model," Translational Lung Cancer Research, Nov. 2021, vol. 10 (11), pp. 4152-4160.
Linte, C.A., et al., "Inside the Beating Heart: An in Vivo Feasibility Study on Fusing Pre- and Intra-Operative Imaging for Minimally Invasive Therapy", International Journal of Computer Assisted Radiology and Surgery [Online], 2009, vol. 4, No. 2, pp. 113-123.
Linte, C.A., et al., "Virtual and Augmented Medical Imaging Environments: Enabling Technology for Minimally Invasive Cardiac Interventional Guidance", IEEE Reviews in Biomedical Engineering, 2010, vol. 3, pp. 25-47.
Maier-Hein, L., et al., "Surgical Data Science—From Concepts Toward Clinical Translation," Arxiv.Org, Cornell University Library, 201 Olin Library Cornell University Ithaca, NY 14853, Jul. 30, 2021.
Robb, A., "Using Patient Specific Anatomic Models", IEEE Engineering in Medicine and Biology Magazine, IEEE Service Center, Pisacataway, 1996, vol. 15, No. 2, pp. 60-69.
Silva., et al., Medical Imaging Archiving: A Comparison between Several NoSQL Solutions, IEEE EMBS International Conference on Information Technology Applications in Biomedicine (ITAB), 5 pages.
Suematsu, Y., et al., "Robotic-Assisted Closure of Atrial Septal Defect Under Real-Time Three-Dimensional Echo Guide: In Vitro Study", European Journal of Cardio-Thoracic Surgery, Springer Verlag, Beriln, 2007, vol. 32, No. 4, pp. 573-576.
U.S. Final Office Action dated Oct. 16, 2024 in U.S. Appl. No. 17/974,689.
U.S. Non-Final Office Action dated Dec. 14, 2023 in U.S. Appl. No. 17/334,487.
U.S. Non-Final Office Action dated May 2, 2024 in U.S. Appl. No. 17/974,689.
U.S. Non-Final Office Action dated Sep. 10, 2024 in U.S. Appl. No. 17/955,941.
U.S. Notice of Allowance dated Apr. 17, 2024 in U.S. Appl. No. 17/334,487.
U.S. Restriction requirement dated Jun. 20, 2024, in U.S. Appl. No. 17/955,941.
Zhang, Q., et al., "Dynamic Real-Time 4D Cardiac MDCT Image Display using GPU-Accelerated Volume Rendering", Computerized Medical Imaging and Graphics, Pergamon Press, 2009, vol. 33, No. 6, pp. 461-476.
U.S. Final Office Action dated Mar. 18, 2025 in U.S. Appl. No. 17/955,941.
U.S. Non-Final Office Action dated Mar. 6, 2025 in U.S. Appl. No. 17/999,983.
U.S. Non-Final Office Action dated Mar. 11, 2025 in U.S. Appl. No. 17/999,986.
U.S. Advisory Action dated May 29, 2025 in U.S. Appl. No. 17/955,941.
U.S. Notice of Allowance dated Jul. 29, 2025 in U.S. Appl. No. 17/999,983.
U.S. Final Office Action dated Aug. 22, 2025 in U.S. Appl. No. 17/999,986.
U.S. Non-Final Office Action dated Sep. 24, 2025 in U.S. Appl. No. 17/955,941.

* cited by examiner

300

Figure 4A:
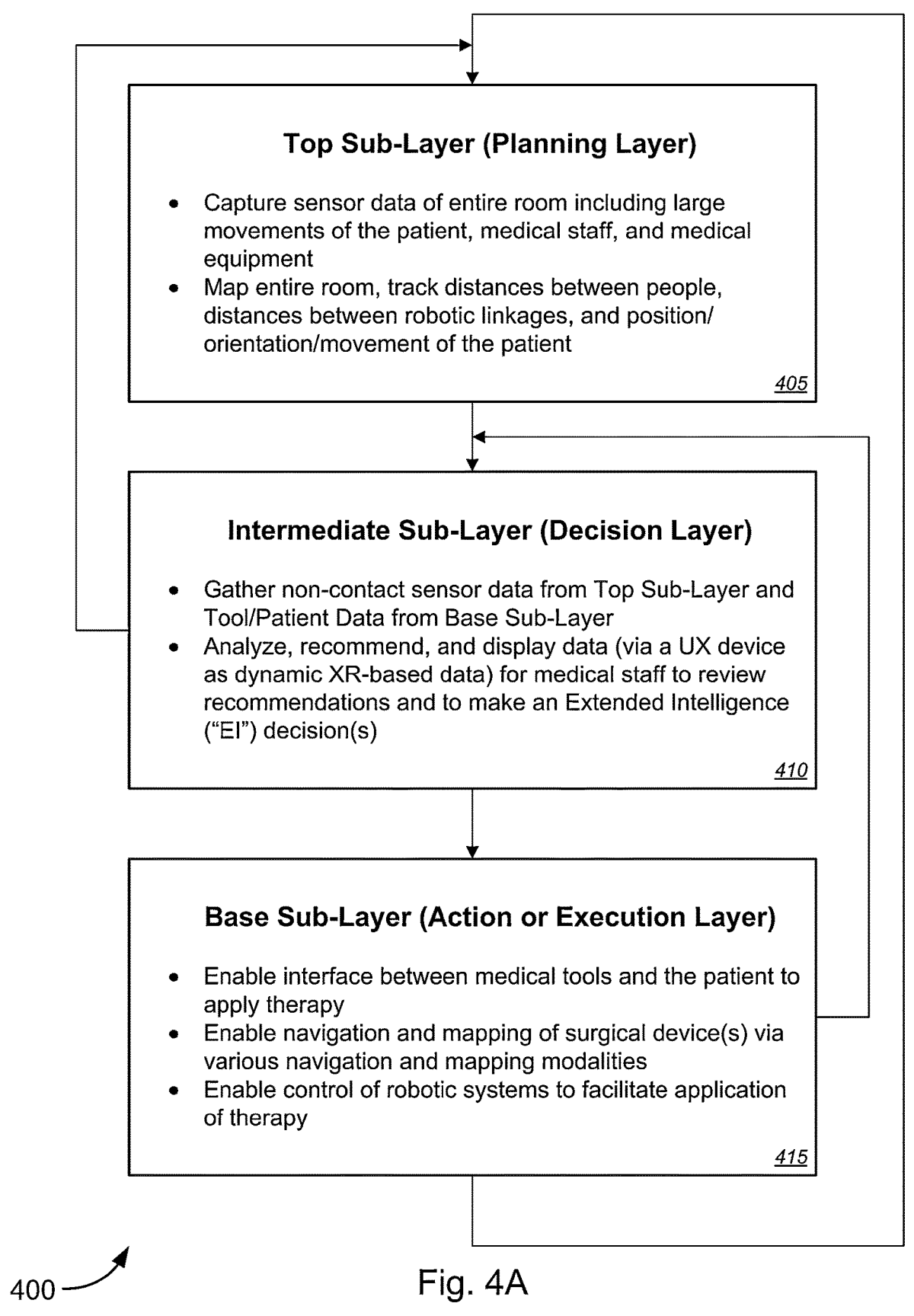

Top Sub-Layer (Planning Layer)

- Capture sensor data of entire room including large movements of the patient, medical staff, and medical equipment
- Map entire room, track distances between people, distances between robotic linkages, and position/orientation/movement of the patient

*405*

Intermediate Sub-Layer (Decision Layer)

- Gather non-contact sensor data from Top Sub-Layer and Tool/Patient Data from Base Sub-Layer
- Analyze, recommend, and display data (via a UX device as dynamic XR-based data) for medical staff to review recommendations and to make an Extended Intelligence ("EI") decision(s)

*410*

Base Sub-Layer (Action or Execution Layer)

- Enable interface between medical tools and the patient to apply therapy
- Enable navigation and mapping of surgical device(s) via various navigation and mapping modalities
- Enable control of robotic systems to facilitate application of therapy

Pre-Operative Planning

_420_

Intra-Operative Adjustments

_425_

Post-Operative Monitoring & Optimization
Feedback

_430_

400'

500

500

700

Ⓐ

Ⓑ

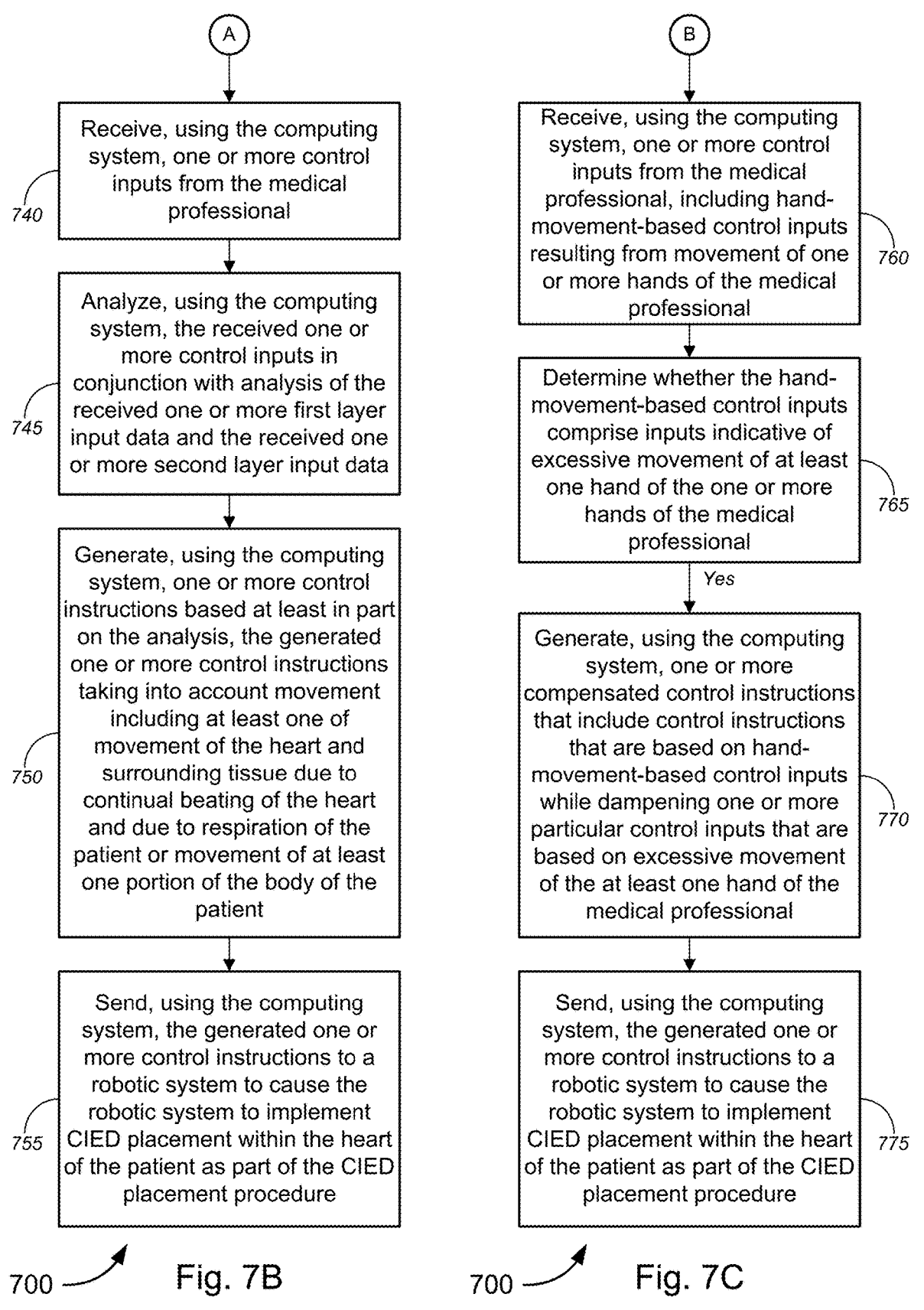

740 → Receive, using the computing system, one or more control inputs from the medical professional 760 → Receive, using the computing system, one or more control inputs from the medical professional, including hand-movement-based control inputs resulting from movement of one or more hands of the medical professional 745 → Analyze, using the computing system, the received one or more control inputs in conjunction with analysis of the received one or more first layer input data and the received one or more second layer input data 765 → Determine whether the hand-movement-based control inputs comprise inputs indicative of excessive movement of at least one hand of the one or more hands of the medical professional Yes 750 → Generate, using the computing system, one or more control instructions based at least in part on the analysis, the generated one or more control instructions taking into account movement including at least one of movement of the heart and surrounding tissue due to continual beating of the heart and due to respiration of the patient or movement of at least one portion of the body of the patient 770 → Generate, using the computing system, one or more compensated control instructions that include control instructions that are based on hand-movement-based control inputs while dampening one or more particular control inputs that are based on excessive movement of the at least one hand of the medical professional 755 → Send, using the computing system, the generated one or more control instructions to a robotic system to cause the robotic system to implement CIED placement within the heart of the patient as part of the CIED placement procedure 775 → Send, using the computing system, the generated one or more control instructions to a robotic system to cause the robotic system to implement CIED placement within the heart of the patient as part of the CIED placement procedure 700 ⟋   Fig. 7B 700 ⟋   Fig. 7C

800

EXTENDED INTELLIGENCE FOR CARDIAC IMPLANTABLE ELECTRONIC DEVICE (CIED) PLACEMENT PROCEDURES

CROSS-REFERENCE TO RELATED APPLICATIONS

This application claims priority to U.S. Patent Application Ser. No. 63/187,738 (the "'738 application"), filed May 12, 2021, by Peter N. Braido et al., entitled, "Extended Intelligence for Cardiac Implantable Electronic Device (CIED) Placement Procedures," the disclosure of which is incorporated herein by reference in its entirety for all purposes.

This application may also be related to each of U.S. Patent Application Ser. No. 63/032,278 (the "'278 application"), filed May 29, 2020 by Peter N. Braido et al., entitled, "Intelligent Assistance (IA) Ecosystem," U.S. Patent Application Ser. No. 63/032,283 (the "'283 application"), filed May 29, 2020 by Peter N. Braido et al., entitled, "Extended Reality (XR) Applications for Cardiac Arrhythmia Procedures," U.S. Patent Application Ser. No. 63/032,289 (the "'289 application"), filed May 29, 2020 by Peter N. Braido et al., entitled, "Extended Reality (XR) Applications for Cardiac Blood Flow Procedures," and U.S. Patent Application Ser. No. 63/058,632 (the "'632 application"), filed Jul. 30, 2020 by Peter Braido et al., entitled, "Extended Reality (XR) Applications for Cardiac Shunting Procedures," the disclosure of each of which is incorporated herein by reference in its entirety for all purposes.

The respective disclosures of these applications/patents (which this document refers to collectively as the "Related Applications") are incorporated herein by reference in their entirety for all purposes.

FIELD

The present disclosure relates, in general, to methods, systems, and apparatuses for implementing medical assistance technologies, and, more particularly, to methods, systems, and apparatuses for implementing intelligent assistance ("IA") or extended intelligence ("EI") ecosystem, and even more particularly, to methods, systems, and apparatuses for implementing extended intelligence to placement procedures for cardiac implantable electronic device ("CIED") for cardiac sensing and pacing.

BACKGROUND

There are many untreated patients with arrhythmias currently. For example, 30% of patients undergoing cardiac resynchronization therapy ("CRT") are classified as non-responders, and conventional right ventricular pacing ("RVP") is associated with a risk of heart failure and atrial fibrillation.

Traditionally, during medical operations or placement procedures of cardiac implantable electronic devices ("CIEDs") for cardiac sensing and pacing (such as CRT, RVP, His-Purkinje system pacing device placement, or CIED placement procedures in general, or the like), a surgeon or other medical professional would perform the operation or procedure by hand or using (then up-to-date) surgical tools and instruments, with any imaging and mapping of the progress of the operation or procedure being divorced from or otherwise separate from use of the surgical tools and instruments. This leads to significant effort on the medical professional to fully grasp the situation while juggling the difficulties of the operation or procedure itself, which may lead to complications or issues during the operation or procedure, particularly for complex ones. In some cases, this may also lead to cognitive overload for the medical professional, as well as the medical professional literally not having enough hands to operate all the tools. In addition, such traditional techniques typically rely on use of fluoroscopy and/or contrast, which introduces risks to the patient, the physician(s), and/or the staff due to radiation exposure. Other disadvantages or issues with traditional techniques include imaging data lacking in information that the physician needs for 3D placement of CIEDs, lack of compensation for beating heart and respiration of the patient as well as excessive hand movements of the physician, adverse events caused by inaccurate placement such as pocket hematoma, pneumothorax, lead dislodgment, or pericardial effusion, and/or the like.

More recently, the use of augmented reality or mixed reality to aid in the medical professional during operations or procedures has led to improvements in the system, allowing for more successful outcomes to the operations or procedures. Such recent developments, however, do not fully implement compilation of surgical tool or instrument data, imaging data, and patient data, or integrate the compilation of such data with data analytics and artificial intelligence ("AI") or machine learning or deep learning, and with an intuitive extended reality ("XR") implementation, and, in some cases, also with interfacing robotics to achieve an intelligent assistance ("IA") or extended intelligence ("EI") ecosystem as described in detail below.

Hence, there is a need for more robust and scalable solutions for implementing medical assistance technologies, and, more particularly, to methods, systems, and apparatuses for implementing intelligent assistance ("IA") or extended intelligence ("EI") ecosystem, and even more particularly, to methods, systems, and apparatuses for implementing extended intelligence to placement procedures for cardiac implantable electronic device ("CIED") for cardiac sensing and pacing.

SUMMARY

The techniques of this disclosure generally relate to tools and techniques for implementing medical assistance technologies, and, more particularly, to methods, systems, and apparatuses for implementing intelligent assistance ("IA") or extended intelligence ("EI") ecosystem, and even more particularly, to methods, systems, and apparatuses for implementing extended intelligence to placement procedures for cardiac implantable electronic device ("CIED") for cardiac sensing and pacing.

In an aspect, a method may comprise receiving, using a computing system, one or more first layer input data from one or more first devices, the one or more first layer input data comprising at least one of movement data, position data, relative distance data, or externally observable data for each of one or more persons and one or more objects within a room; and receiving, using the computing system, one or more second layer input data from one or more second devices, the one or more second layer input data comprising at least one of one or more patient sensor data for monitoring procedure-relevant aspects of a patient, one or more patient imaging data for monitoring images of one or more portions of a body of the patient, or one or more navigation and mapping data for monitoring one or more surgical devices relative to the one or more portions of the body of the patient. The method may also comprise analyzing, using the computing system, the received one or more first layer input data and the received one or more second layer input; and generating, using the computing system, one or more recommendations for guiding a medical professional in performing a cardiac implantable electronic device ("CIED") placement procedure in a heart of the patient, based at least in part on the analysis, the generated one or more recommendations comprising three-dimensional ("3D") or four-dimensional ("4D") mapped guides toward, in, and around the heart of the patient. The method may further comprise generating, using the computing system, one or more extended reality ("XR") images, based at least in part on the generated one or more recommendations; and presenting, using the computing system and using a user experience ("UX") device, the generated one or more XR images.

In some embodiments, the computing system may comprise at least one of an XR computing system, a medical procedure computing system, a hub computing system, a 3D graphical processing unit, a cluster computing system, a 4D graphics computing system, a server computer, a cloud computing system, or a distributed computing system, and/or the like.

According to some embodiments, the one or more surgical devices may comprise at least one of one or more catheters, one or more catheter interconnect cables, one or more leads, one or more pacemakers, one or more defibrillators, one or more rigid robotic devices, one or more soft robotic devices, one or more robotic systems, one or more robotic arms, one or more needles, one or more therapeutic delivery devices, one or more implant delivery devices, one or more diagnostic devices, one or more diagnostic catheters, one or more implant devices, one or more surgical tools, one or more monitoring devices, one or more cameras, one or more imaging tools, one or more fiducials, one or more staples, one or more anchors, one or more embolic protection devices, one or more cardiomyoplasty tools, one or more vascular closure tools, one or more septal closure tools, one or more guide wires, one or more introducers, one or more sheaths, an implantable cardioverter defibrillator ("ICD") device, an extravascular ICD ("EV-ICD"), a miniature leadless implant, a conduction system pacing ("CSP") device, an implantable bradycardia pacemaker with leads, a leadless bradycardia pacemaker, a low power implantable cardiac resynchronization therapy ("CRT-P") device, a high power implantable cardiac resynchronization therapy ("CRT-D") device, or one or more capital equipment, and/or the like.

In some embodiments, the one or more patient sensor data may be obtained using one or more sensors comprising at least one of one or more chronically implanted sensors, one or more diagnostic sensors, one or more surgical sensors, one or more wearable sensors, one or more gas sensors, one or more optical sensors, one or more impedance sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more motion sensors, one or more sound sensors, one or more blood pressure sensors, one or more heart rate sensors, one or more pulse sensors, one or more oxygen sensors, one or more carbon dioxide ("CO$_2$") sensors, one or more fluid levels, one or more doppler sensors, one or more biomarker sensors, one or more perfusion sensors, one or more electromyography ("EMG") sensors, one or more sleep sensors, one or more cardiac hemodynamics sensors, one or more ischemia sensors, one or more hematocrit ("HCT") level sensors, one or more biometric sensors, one or more electroencephalographic ("EEG") sensors, or one or more pain sensors, and/or the like.

According to some embodiments, the one or more patient imaging data may be obtained using one or more imaging devices comprising at least one of a magnetic resonance imaging ("MRI") system, a computed tomography ("CT") system, an ultrasound ("US") system, an electromechanical wave imaging ("EWI") system, a magnetic resonance angiography ("MRA") system, a computed tomography angiography ("CTA") system, a blood oxygen-level dependent signal ("BOLD") system, an electroencephalography ("EEG") system, an optical coherence tomography ("OCT") system, a dynamic susceptibility contrast ("DSC") MRI system, a fluoroscopy system, an X-ray system, or an endoscopy system, and/or the like.

In some instances, the CIED placement procedure may comprise at least one of a cardiac mapping procedure, a cardiac resynchronization therapy ("CRT") device installation procedure, a right ventricular pacing ("RVP") procedure, a His bundle pacing ("HBP") procedure, a left bundle branch pacing ("LBBP") lead placement procedure, a right bundle branch pacing ("RBBP") lead placement procedure, a bilateral bundle branch area pacing "(BBBP") lead placement procedure, an implant procedure, an implantable cardioverter defibrillator ("ICD") device installation procedure, an extravascular ICD ("EV-ICD") device installation procedure, a pacemaker installation procedure, a miniature leadless implant installation procedure, or a remote monitoring device installation procedure, and/or the like.

In some cases, the one or more XR images may comprise at least one of one or more augmented reality ("AR") images, one or more AR videos, one or more virtual reality ("VR") images, one or more VR videos, one or more mixed reality ("MR") images, one or more MR videos, one or more XR images, or one or more XR videos, and/or the like.

In some embodiments, the UX device may comprise at least one of a headset, UX glasses, a viewing window, a supplement to existing glasses, headphones, UX contact lenses, a heads-up display ("HUD") device, a 3D spatial sound system, a telemonitoring system, a rigid robotic device control and sensory feedback system, a soft robotic device control and sensory feedback system, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a 3D printed reconstruction system, a customized view generation system, a ghosting and prediction system, a master-slave control system, an annotation system, or a haptic feedback system, and/or the like.

In some instances, the generated one or more XR images may be presented to provide one or more of: a guide for the medical professional, a navigation tool during the CIED placement procedure, a proximity detection tool during the CIED placement procedure, a 3D or 4D visualization view of the at least one or more portions of the patient, a heads-up display of at least one of the one or more first layer input data, a heads-up display of at least one of the one or more patient sensor data, a heads-up display of at least one of the one or more patient imaging data, a heads-up display of physiological data of the patient, or a heads-up display of procedure-related data of the patient, and/or the like.

According to some embodiments, the method may further comprise tracking, using the computing system, the one or more surgical devices, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

In some embodiments, the method may further comprise receiving, using the computing system, one or more control inputs from the medical professional; analyzing, using the computing system, the received one or more control inputs in conjunction with analysis of the received one or more first layer input data and the received one or more second layer input data; generating, using the computing system, one or more control instructions based at least in part on the analysis, the generated one or more control instructions taking into account movement including at least one of movement of the heart and surrounding tissue due to continual beating of the heart and due to one or more of table movement, fluid loss, respiration of the patient, or movement or shifting of at least one portion of the body of the patient; and sending, using the computing system, the generated one or more control instructions to a robotic system to cause the robotic system to implement CIED placement within the heart of the patient as part of the CIED placement procedure.

In some cases, at least the processes of receiving the one or more first layer input data, the one or more second layer input data, analyzing the received one or more first layer input data and the received one or more second layer input, generating the one or more recommendations, generating the one or more XR images, presenting the generated one or more XR images, receiving the one or more control inputs, analyzing the received one or more control inputs, generating the one or more control instructions, and sending the generated one or more control instructions may occur in a manner that is at least one of continual, dynamic, feedback-looped, updated, in real-time, or in near-real-time, and/or the like, during the course of the CIED placement procedure.

Alternatively, or additionally, the received one or more control inputs may comprise hand-movement-based control inputs resulting from movement of one or more hands of the medical professional, wherein analyzing the received one or more control inputs may comprise determining whether the hand-movement-based control inputs comprise inputs indicative of excessive movement of at least one hand of the one or more hands of the medical professional, and wherein generating the one or more control instructions may comprise, based on a determination that the hand-movement-based control inputs comprise inputs indicative of excessive movement of at least one hand of the medical professional, generating, using the computing system, one or more compensated control instructions that include control instructions that are based on hand-movement-based control inputs while dampening one or more particular control inputs that are based on excessive movement of the at least one hand of the medical professional.

According to some embodiments, the method may be performed without use of fluoroscopy.

In another aspect, an apparatus might comprise at least one processor and a non-transitory computer readable medium communicatively coupled to the at least one processor. The non-transitory computer readable medium might have stored thereon computer software comprising a set of instructions that, when executed by the at least one processor, causes the apparatus to: receive one or more first layer input data from one or more first devices, the one or more first layer input data comprising at least one of movement data, position data, relative distance data, or externally observable data for each of one or more persons and one or more objects within a room; receive one or more second layer input data from one or more second devices, the one or more second layer input data comprising at least one of one or more patient sensor data for monitoring procedure-relevant aspects of a patient, one or more patient imaging data for monitoring images of one or more portions of a body of the patient, or one or more navigation and mapping data for monitoring one or more surgical devices relative to the one or more portions of the body of the patient; analyze the received one or more first layer input data and the received one or more second layer input; generate one or more recommendations for guiding a medical professional in performing a cardiac implantable electronic device ("CIED") placement procedure in a heart of the patient, based at least in part on the analysis, the generated one or more recommendations comprising three-dimensional ("3D") or four-dimensional ("4D") mapped guides toward, in, and around the heart of the patient; generate one or more extended reality ("XR") images, based at least in part on the generated one or more recommendations; and present, using a user experience ("UX") device, the generated one or more XR images.

In yet another aspect, a system might comprise a computing system, which might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the computing system to: receive one or more first layer input data from one or more first devices, the one or more first layer input data comprising at least one of movement data, position data, relative distance data, or externally observable data for each of one or more persons and one or more objects within a room; receive one or more second layer input data from one or more second devices, the one or more second layer input data comprising at least one of one or more patient sensor data for monitoring procedure-relevant aspects of a patient, one or more patient imaging data for monitoring images of one or more portions of a body of the patient, or one or more navigation and mapping data for monitoring one or more surgical devices relative to the one or more portions of the body of the patient; analyze the received one or more first layer input data and the received one or more second layer input; generate one or more recommendations for guiding a medical professional in performing a cardiac implantable electronic device ("CIED") placement procedure in a heart of the patient, based at least in part on the analysis, the generated one or more recommendations comprising three-dimensional ("3D") or four-dimensional ("4D") mapped guides toward, in, and around the heart of the patient; generate one or more extended reality ("XR") images, based at least in part on the generated one or more recommendations; and present, using a user experience ("UX") device, the generated one or more XR images.

Various modifications and additions can be made to the embodiments discussed without departing from the scope of the invention. For example, while the embodiments described above refer to particular features, the scope of this invention also includes embodiments having different combination of features and embodiments that do not include all of the above-described features.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIG. 4A is a flow diagram illustrating a non-limiting example of feedbacked interactions among three sub-layers of imbedded and contactless sensors, data, and vision systems that may be used as part of an IA or EI ecosystem implementation for CIED placement procedures, in accordance with various embodiments.

FIGS. 7A-7C are flow diagrams illustrating a method for implementing an IA or EI ecosystem for CIED placement procedures, in accordance with various embodiments.

Figure 1:
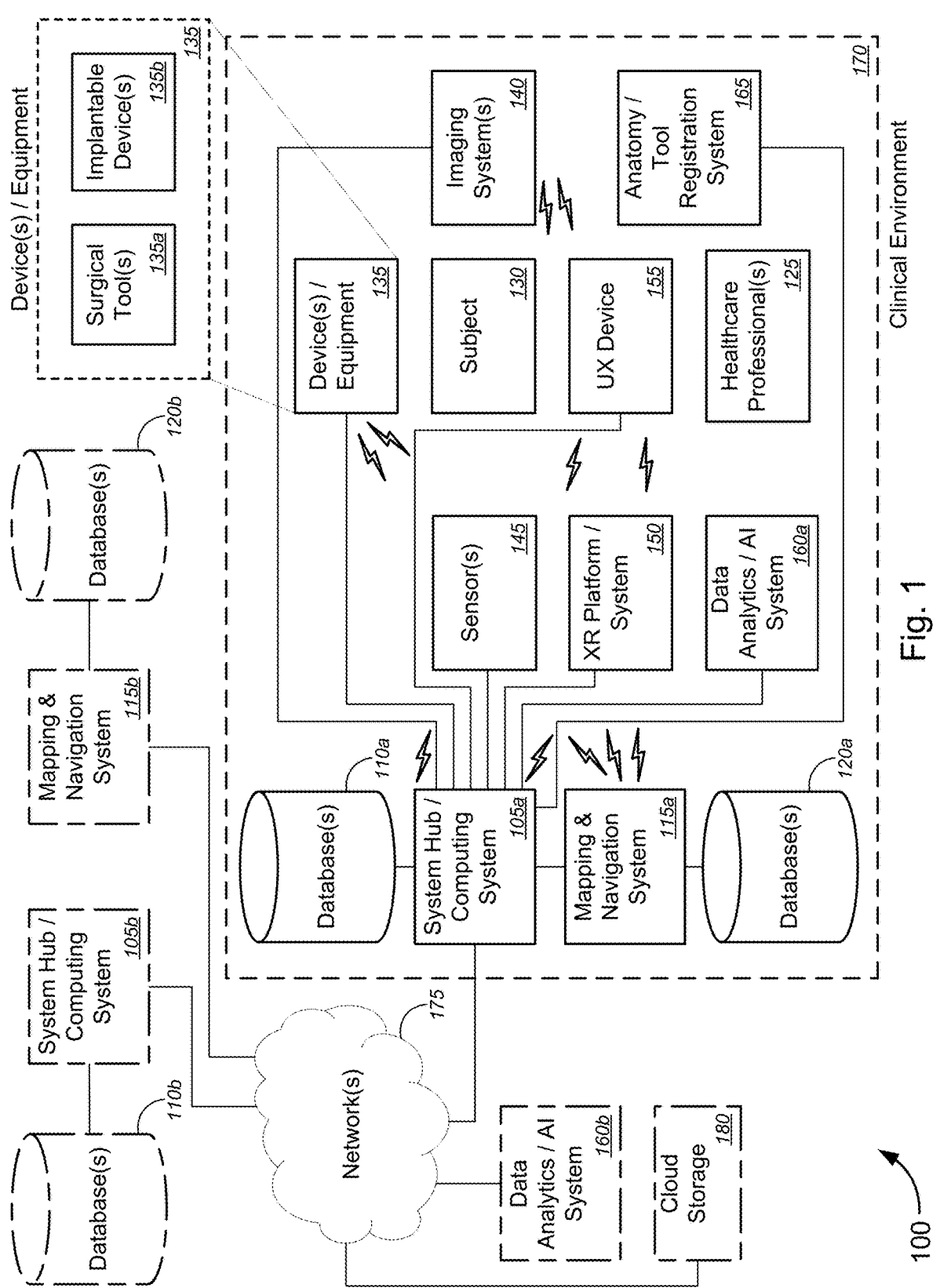
FIG. 1 is a schematic diagram illustrating a system for implementing an intelligent assistance ("IA") or extended intelligence ("EI") ecosystem for cardiac implantable electronic device ("CIED") placement procedures, in accordance with various embodiments.

DETAILED DESCRIPTION OF CERTAIN
EMBODIMENTS

Overview

In various embodiments, a computing system might receive one or more first layer input data from one or more first devices, the one or more first layer input data comprising at least one of movement data, position data, relative distance data, or externally observable data for each of one or more persons and one or more objects within a room. The computing system might receive one or more second layer input data from one or more second devices, the one or more second layer input data comprising at least one of one or more patient sensor data for monitoring procedure-relevant aspects of a patient, one or more patient imaging data for monitoring images of one or more portions of a body of the patient, or one or more navigation and mapping data for monitoring one or more surgical devices relative to the one or more portions of the body of the patient, and/or the like.

The computing system might analyze the received one or more first layer input data and the received one or more second layer input, and might generate one or more recommendations for guiding a medical professional in performing a cardiac implantable electronic device ("CIED") placement procedure in a heart of the patient, based at least in part on the analysis, the generated one or more recommendations comprising three-dimensional ("3D") or four-dimensional ("4D") mapped guides toward, in, and around the heart of the patient. The computing system might then generate one or more XR images (or one or more XR experiences), based at least in part on the generated one or more recommendations, and might present the generated one or more XR images (or one or more XR experiences) using a UX device.

According to some embodiments, the generated one or more XR images might be presented to provide one or more of: a guide for a medical professional, a navigation tool during the CIED placement procedure, a proximity detection tool during the CIED placement procedure, a 3D or 4D visualization view of the at least one or more portions of the patient, a heads-up display of at least one of the one or more first layer input data, a heads-up display of at least one of the one or more patient sensor data, a heads-up display of at least one of the one or more patient imaging data, a heads-up display of physiological data of the patient, or a heads-up display of procedure-related data of the patient, and/or the like. In some instances, generating the one or more XR images might comprise combining or mapping the received one or more first layer input data and the received one or more second layer input into a combined 3D or 4D representation, based at least in part on the analysis and the generated one or more recommendations; and generating the one or more XR images based on the combined 3D or 4D representation.

According to some embodiments, the computing system might receive one or more control inputs from the medical professional; might analyze the received one or more control inputs in conjunction with analysis of the received one or more first layer input data and the received one or more second layer input data; might generate one or more control instructions based at least in part on the analysis, the generated one or more control instructions taking into account movement including at least one of movement of the heart and surrounding tissue due to continual beating of the heart and due to one or more of table movement, fluid loss, respiration of the patient, or movement or shifting of at least one portion of the body of the patient; and might send the generated one or more control instructions to a robotic system to cause the robotic system to implement CIED placement within the heart of the patient as part of the CIED placement procedure. Herein, CIEDs may refer to cardiac implantable electronic devices with or without leads, which may be evident from express description of such or based on context. In the absence of either express description or suitable context, CIEDs may refer to the versions of the CIEDs either with or without leads.

In some instances, at least the processes of receiving the one or more first layer input data, the one or more second layer input data, analyzing the received one or more first layer input data and the received one or more second layer input, generating the one or more recommendations, generating the one or more XR images, presenting the generated one or more XR images, receiving the one or more control inputs, analyzing the received one or more control inputs, generating the one or more control instructions, and/or sending the generated one or more control instructions may occur in a manner that is at least one of continual, dynamic, feedback-looped, updated, in real-time, or in near-real-time, and/or the like, during the course of the CIED placement procedure.

In some embodiments, the received one or more control inputs may comprise hand-movement-based control inputs resulting from movement of one or more hands of the medical professional. In such cases, analyzing the received one or more control inputs may comprise determining whether the hand-movement-based control inputs comprise inputs indicative of excessive movement of at least one hand of the one or more hands of the medical professional. As such, generating the one or more control instructions may comprise, based on a determination that the hand-movement-based control inputs comprise inputs indicative of excessive movement of at least one hand of the medical professional, the computing system generating one or more compensated control instructions that include control instructions that are based on hand-movement-based control inputs while dampening one or more particular control inputs that are based on excessive movement of the at least one hand of the medical professional.

In various aspects, decision support systems (i.e., Extended Intelligence or EI systems) are supporting clinicians at an ever-increasing rate, which has been bolstered by advances in machine learning, contactless sensors, robotics, and extended reality (among other parts of the ecosystem as shown and described with respect to the figures). These decision support systems enable seamless integration of the complex workflows, equipment, and devices so augmented clinical decision-making affords the patient with safer, more efficacious, consistent, and timely outcomes.

Most physical workspaces are sensitive and responsive to the non-contact and contact interactions between humans and the medical equipment in such workspaces, so by gathering this data without interfering with the workflow via contactless sensors, analyzing via machine learning algorithms, then displaying what is needed at the right time and place via extended reality systems (at least in part) will avoid medical staff cognitive overload, inefficiencies, and sub-optimal outcomes (i.e., inaccurate or imprecise placement of CIEDs), or the like. The IA or EI ecosystem may also compensate for beating heart and respiration of the patient as well as excessive movement of the user or physician, while reducing or eliminating the use of fluoroscopy and contrast.

These and other aspects of the extended intelligence for CIED placement procedures are described in greater detail with respect to the figures.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Various embodiments described herein, while embodying (in some cases) software products, computer-performed methods, and/or computer systems, represent tangible, concrete improvements to existing technological areas, including, without limitation, medical operation technology, medical procedure technology, medical imaging technology, medical visualization and mapping technology, medical assistance technology, and/or the like. In other aspects, certain embodiments, can improve the functioning of user equipment or systems themselves (e.g., medical operation system, medical procedure system, medical imaging system, medical visualization and mapping system, medical assistance system, etc.), for example, by receiving, using a computing system, one or more first layer input data from one or more first devices, the one or more first layer input data comprising at least one of movement data, position data, relative distance data, or externally observable data for each of one or more persons and one or more objects within a room; receiving, using the computing system, one or more second layer input data from one or more second devices, the one or more second layer input data comprising at least one of one or more patient sensor data for monitoring procedure-relevant aspects of a patient, one or more patient imaging data for monitoring images of one or more portions of a body of the patient, or one or more navigation and mapping data for monitoring one or more surgical devices relative to the one or more portions of the body of the patient; analyzing, using the computing system, the received one or more first layer input data and the received one or more second layer input; generating, using the computing system, one or more recommendations for guiding a medical professional in performing a cardiac implantable electronic device ("CIED") placement procedure in a heart of the patient, based at least in part on the analysis, the generated one or more recommendations comprising three-dimensional ("3D") or four-dimensional ("4D") mapped guides toward, in, and around the heart of the patient; generating, using the computing system, one or more extended reality ("XR") images, based at least in part on the generated one or more recommendations; and presenting, using the computing system and using a user experience ("UX") device, the generated one or more XR images; and/or the like.

In particular, to the extent any abstract concepts are present in the various embodiments, those concepts can be implemented as described herein by devices, software, systems, and methods that involve specific novel functionality (e.g., steps or operations), such as, implementing an intelligent assistance ("IA") or extended intelligence ("EI") ecosystem that receives and combines the one or more first layer input data (i.e., room content-based data) and the one or more second layer input data (i.e., patient and/or tool-based data); that analyzes these data and generates recommendations for guiding a medical professional in performing a cardiac implantable electronic device ("CIED") placement procedure in a heart of the patient, based at least in part on the analysis; that generates the one or more XR images; and that presents (using the UX device) the generated one or more XR images, and/or the like, to name a few examples, that extend beyond mere conventional computer processing operations. These functionalities can produce tangible results outside of the implementing computer system, including, merely by way of example, optimized and comprehensive IA or EI ecosystem that achieves better safety and efficacy (i.e., compensating for beating heart and respiration of the patient as well as excessive movement of the user or physician, while reducing or eliminating the use of fluoroscopy and contrast, etc.), while reducing costs of operation of the system, increasing throughput of procedures, providing predictable procedure durations, reducing cognitive overload for the physician, increasing longevity of physician careers (e.g., by wearing lead during fluoroscopy), and/or the like, at least some of which may be observed or measured by users, patients, and/or service providers.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Specific Exemplary Embodiments

We now turn to the embodiments as illustrated by the drawings. FIGS. 1-9 illustrate some of the features of the method, system, and apparatus for implementing medical assistance technologies, and, more particularly, to methods, systems, and apparatuses for implementing intelligent assistance ("IA") or extended intelligence ("EI") ecosystem, and even more particularly, to methods, systems, and apparatuses for implementing extended intelligence to placement procedures for cardiac implantable electronic device ("CIED") for cardiac sensing and pacing, as referred to above. The methods, systems, and apparatuses illustrated by FIGS. 1-9 refer to examples of different embodiments that include various components and steps, which can be considered alternatives or which can be used in conjunction with one another in the various embodiments. The description of the illustrated methods, systems, and apparatuses shown in FIGS. 1-9 is provided for purposes of illustration and should not be considered to limit the scope of the different embodiments.

With reference to the figures, FIG. 1 is a schematic diagram illustrating a system 100 for implementing an intelligent assistance ("IA") or extended intelligence ("EI") ecosystem for cardiac implantable electronic device ("CIED") placement procedures (or more specifically, cardiac sense/stimulation electrode placement procedures, or the like), in accordance with various embodiments. Herein, CIEDs may refer to cardiac implantable electronic devices with or without leads, which may be evident from express description of such or based on context. In the absence of either express description or suitable context, CIEDs may refer to the versions of the CIEDs either with or without leads.

In the non-limiting embodiment of FIG. 1, system 100 might comprise a system hub or computing system 105a and corresponding database(s) 110a. In some cases, the database(s) 110a may be local to the system hub or computing system 105a. In some cases, the database(s) 110a may be external, yet communicatively coupled to the system hub or computing system 105a. In other cases, the database(s) 110a may be local and integrated within the system hub or computing system 105a. System 100, according to some embodiments, might further comprise mapping and navigation system 115a and corresponding database(s) 120a. Like database(s) 110a, the database(s) 120a may be local to the mapping and navigation system 115a. In some cases, the database(s) 120a may be external, yet communicatively coupled to the mapping and navigation system 115a. In other cases, the database(s) 120a may be local and integrated within the mapping and navigation system 115a.

System 100 might include, without limitation, at least one of one or more healthcare professionals 125, a subject 130, one or more devices or equipment 135, one or more imaging systems 140, one or more sensors 145, an extended reality ("XR") platform or system 150, a user experience ("UX") device 155, a data analytics or artificial intelligence ("AI") system 160a, or an anatomy or tool registration system 165, and/or the like. In some instances, the system hub or computing system 105a and corresponding database(s) 110a, the mapping and navigation system 115a and corresponding database(s) 120a, and the at least one of the one or more healthcare professionals 125, the subject 130, the one or more devices or equipment 135, the one or more imaging systems 140, the one or more sensors 145, the XR platform or system 150, the UX device 155, the data analytics or AI system 160a, or the anatomy or tool registration system 165, and/or the like, may be located or disposed within clinical environment 170. In some cases, the clinical environment 170 might include, but is not limited to, a clinic, a hospital, an operating room, an emergency room, a physician's office, or a laboratory, or the like.

In some embodiments, the system hub or computing system 105a might include, without limitation, at least one of an XR computing system, a medical procedure computing system, a hub computing system, a three-dimensional ("3D") graphical processing unit, a cluster computing system, a four-dimensional ("4D") graphics computing system, a server computer, a cloud computing system, or a distributed computing system, and/or the like. In some instances, the one or more healthcare professionals 125 might include, without limitation, at least one of one or more doctors, one or more surgeons, one or more cardiologists, one or more electrophysiologists, one or more cardiac surgeons, one or more neurosurgeons, one or more radiologists, one or more scenographers, one or more nurse practitioners, one or more nurses, one or more medical specialists, one or more medical imaging specialists, and/or the like. In some cases, the subject 130 might include, but is not limited to, one of a human patient; a large animal (e.g., pig, sheep, dog, etc.); a small animal (e.g., rabbit, rat, mouse, etc.); an organ (e.g., explant, transplant, decellularized, deceased, generated, synthetic, etc.); an organelle; one or more organs on a chip; one or more tissue constructs; one or more cells; one or more microbes of bacterial vectors; one or more microbes of viral vectors; one or more microbes of prion vectors; one or more genes, deoxyribonucleic acid ("DNA"), ribonucleic acid ("RNA"); one or more hormones, one or more biochemicals, one or more molecules; one or more tissues, one or more blood vessels, or one or more bones; and/or the like.

According to some embodiments, the one or more devices or equipment 135—which might include surgical tool(s)/device(s) 135a, implantable device(s) 135b, or the like—might include, but is not limited, at least one of one or more catheters, one or more catheter interconnect or interface cables, one or more leads, one or more pacemakers, one or more defibrillators, one or more neuromodulation devices, one or more neurostimulation devices, one or more rigid robotic devices, one or more soft robotic devices, one or more robotic systems, one or more robotic arms, one or more needles, one or more therapeutic delivery devices, one or more implant delivery devices, one or more diagnostic devices, one or more diagnostic catheters, one or more implant devices, one or more surgical tools, one or more monitoring devices, one or more cameras, one or more imaging tools, one or more fiducials, one or more staples, one or more anchors, one or more embolic protection devices, one or more cardiomyoplasty tools, one or more vascular closure tools, one or more septal closure tools, one or more guide wires, one or more introducers, one or more sheaths, an implantable cardioverter defibrillator ("ICD") device, an extravascular ICD ("EV-ICD"), a miniature leadless implant, one or more implantable sensors (e.g., implantable pulmonary artery sensor(s), or the like), a conduction system pacing ("CSP") device, an implantable bradycardia pacemaker with leads, a leadless bradycardia pacemaker, a low power implantable cardiac resynchronization therapy ("CRT-P") device, a high power implantable cardiac resynchronization therapy ("CRT-D") device, or one or more capital equipment, and/or the like. The one or more devices or equipment 135 might be configured to perform one or more tasks.

In some embodiments, the one or more tasks might include, without limitation, at least one of a surgical procedure, a left atrial appendage ("LAA") procedure, a tissue ablation procedure, a transcatheter aortic valve repair ("TAVr") procedure, a transcatheter aortic valve replacement ("TAVR") procedure (e.g., with the Evolut™ PRO+ TAVR system, or the like), a transcatheter mitral valve repair ("TMVr") procedure, a transcatheter mitral valve replacement ("TMVR") procedure (e.g., with the Intrepid™ TMVR system, or the like), a transcatheter pulmonic valve repair ("TPVr") procedure, a transcatheter pulmonic valve replacement ("TPVR") procedure, a transcatheter tricuspid valve repair ("TTVr") procedure, a transcatheter tricuspid valve replacement ("TTVR") procedure, a mitral clip repair procedure, an implant procedure, a home care ventilation procedure, a lung cancer procedure, an aneurysm flow diversion procedure, a deep brain stimulation procedure, a shunt procedure, a bone grafting procedure, an insulin pump installation procedure, a continuous glucose monitoring system installation procedure, a colon disease procedure, a gastroparesis therapy, a hernia surgery, a bowel control therapy, a microwave ablation procedure, a reflux testing and treatment, a weight-loss surgery, a bone conduction hearing therapy, a sinus surgery, a thyroid surgery, a treatment for ear infections, a balloon angioplasty, a stenting procedure, an atrial septal defect ("ASD") treatment procedure, a cardiac shunt treatment procedure, a heart bypass surgery, a cardiac mapping procedure, a cardiac resynchronization therapy ("CRT") device installation procedure, a catheter ablation procedure, an endovascular repair procedure, a heart monitor installation procedure, an implantable cardioverter defibrillator ("ICD") device installation procedure, an extravascular ICD ("EV-ICD") device installation procedure, a minimally invasive endovascular repair procedure, a pacemaker installation procedure, a miniature leadless implant installation procedure, an implantable sensor installation procedure, a remote monitoring device installation procedure, a surgical heart valve repair and replacement procedure, a transcatheter pulmonary valve ("TPV") therapy (e.g., Melody™ TPV therapy, Harmony™ TPV therapy, or the like), a varicose vein therapy, a ventricular assist device ("VAD") installation procedure, an intra-aortic balloon pump ("IABP") implantation procedure, a heart transplant operation, a back surgery, a bone tumor treatment, a drug pump installation procedure, a spinal cord stimulation procedure, a targeted drug delivery procedure, a balloon kyphoplasty procedure, a cervical disc replacement procedure, a cervical fusion procedure, a sacroiliac joint fusion procedure, a sacral neuromodulation procedure, or a percutaneous tibial neuromodulation procedure, and/or the like.

According to some embodiments, the one or more imaging devices or systems 140 might include, but is not limited to, at least one of a magnetic resonance imaging ("MRI") system, a computed tomography ("CT") system, an ultrasound ("US") system, an electromechanical wave imaging ("EWI") system, a magnetic resonance angiography ("MRA") system, a computed tomography angiography ("CTA") system, a blood oxygen-level dependent signal ("BOLD") system, an electroencephalography ("EEG") system, an optical coherence tomography ("OCT") system, a dynamic susceptibility contrast ("DSC") MRI system, a fluoroscopy system, an X-ray system, or an endoscopy system, and/or the like.

In some embodiments, the one or more sensors 145 might include, without limitation, at least one of one or more chronically implanted sensors, one or more diagnostic sensors, one or more surgical sensors, one or more wearable sensors, one or more gas sensors, one or more optical sensors, one or more impedance sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more motion sensors, one or more sound sensors, one or more blood pressure sensors, one or more heart rate sensors, one or more pulse sensors, one or more oxygen sensors, one or more carbon dioxide ("$CO_2$") sensors, one or more fluid levels, one or more doppler sensors, one or more biomarker sensors, one or more perfusion sensors, one or more electromyography ("EMG") sensors, one or more electrooculography (EOG) sensors, one or more sleep sensors, one or more cardiac hemodynamics sensors, one or more ischemia sensors, one or more hematocrit ("HCT") level sensors, one or more biometric sensors, one or more electroencephalographic ("EEG") sensors, or one or more pain sensors, and/or the like.

According to some embodiments, the XR platform or system 150 might include, without limitation, at least one of an XR headset, a set of XR goggles, a pair of XR-enabled eyewear, an XR-enabled smartphone mounted in a headset, an XR helmet, a mixed reality ("MR") headset, a set of MR goggles, a pair of MR-enabled eyewear, an MR-enabled smartphone mounted in a headset, an MR helmet, a virtual reality ("VR") headset, a set of VR goggles, a pair of VR-enabled eyewear, an VR-enabled smartphone mounted in a headset, an VR helmet, an augmented reality ("AR") headset, a set of AR goggles, a pair of AR-enabled eyewear, an AR-enabled smartphone mounted in a headset, or an AR helmet, and/or the like. Herein, VR might refer to a simulated experience that uses fully virtual constructs generated by a computing system or the like, while AR might refer to an interactive experience of a real-world environment where objects in the real-world are enhanced or augmented by computer-generated perceptual information (in some cases, including visual, auditory, haptic, somatosensory, and/or olfactory information). MR might refer to a merging of the real and virtual worlds to produce new environments and visualizations in which physical and virtual objects co-exist and interact in real-time (in some cases, MR might include AR plus physical interaction and information from the environment that goes beyond just visual aspects, or the like). XR might refer to real and virtual combined environments and human-machine interactions generated by a computing system or the like, and includes AR, MR, and/or VR.

In some instances, the XR platform or system 150 might generate one or more XR experiences including, but not limited to, at least three or more of the one or more XR images, one or more XR sounds, one or more XR haptic or tactile responses, one or more XR simulated smells, or one or more XR simulated tastes, and/or the like, in some cases, based at least in part on the mapping performed by the mapping and navigation system 115a. In some instances, the mapping and navigation system 115a might include, but is not limited to, at least one of an electroanatomic mapping ("EAM") system, an electromagnetic ("EM") mapping and/or navigation system, a radiofrequency identification ("RFID") mapping and/or navigation system, an impedance-based mapping and/or navigation system, an ultrasound ("US") mapping and/or navigation system, an optical mapping and/or navigation system, a high-density mapping catheter (e.g., Achieve™ mapping catheter, Achieve Advance™ mapping catheter, Marinr™ CS mapping catheter, Marinr™ MC mapping catheter, Marinr™ MCXL mapping catheter, Marinr™ SC mapping catheter, StableMapr™ mapping catheter, or the like), one or more patient patches, or navigation hardware and software, and/or the like.

In some embodiments, the UX device 155 might include, without limitation, at least one of a headset, UX glasses, a viewing window, a supplement to existing glasses, headphones, UX contact lenses, a heads-up display ("HUD") device, a 3D spatial sound system, a telemonitoring system, a rigid robotic device control and sensory feedback system, a soft robotic device control and sensory feedback system, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a 3D printed reconstruction system, a customized view generation system, a ghosting and prediction system, a master-slave control system, an annotation system, or a haptic feedback system, and/or the like.

Merely by way of example, in some cases, alternative or additional to the system hub or computing system 105a and corresponding database 110a, the mapping and navigation system 115a and corresponding database 120a, and/or data analytics or AI system 160a being disposed within clinical environment 170, system 100 might comprise remote system hub or computing system 105b and corresponding database(s) 110b, remote mapping and navigation system 115b and corresponding database(s) 120b, and/or data analytics or AI system 160b that communicatively couple with the system hub or computing system 105a (or communications system (not shown)) disposed within the clinical environment 170 via one or more networks 175. According to some embodiments, system 100 might further comprise (optional) cloud storage 180, which communicatively couples with the system hub or computing system 105a via the one or more networks 175. Merely by way of example, network(s) 175 might each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, network(s) 175 might each include an access network of an Internet service provider ("ISP"). In another embodiment, network(s) 175 might each include a core network of the ISP, and/or the Internet.

According to some embodiments, one or more catheter interconnect or interface cables may be used. In some instances, the one or more catheter interconnect or interface cables might include a chip or memory device that is used to store, collect, and transfer data for the XR database. The chip or memory device may also be used to authenticate the device (e.g., as being compatible with the system or as being procedure-qualified, or the like), and may include security features that, when enabled, prevents information from being read or written. For single use devices, this chip or memory device can limit the number of uses to 1. In this manner, the catheter interconnect or interface cables may be used to meet business and/or healthcare requirements: (1) to restrict to single use of a device; (2) to authenticate the device as a real, approved device; (3) to secure the data stored on the device for access by only authorized users; and/or the like. In addition, the catheter interconnect or interface cables may also be used to achieve future additional business and/or healthcare requirements, including, but not limited to: (4) storing, collecting, and/or transferring data for XR applications; and/or the like. To incorporate a chip or memory device into a catheter, the chip or memory device might be mounted on a printed circuit board ("PCB"), which could include other hardware to enable features including, but not limited to: device or procedure sensing (e.g., temperature, orientation, acceleration, position, pressure, humidity, audio record, etc.); wireless communication (e.g., Bluetooth™, network, RFID, etc.); manufacturing and/or device history data storage and transfer to XR information database; and/or the like.

In some aspects, the IA or EI ecosystem, as represented by FIG. 1 for example, might achieve one or more of the following features or functionalities: (1) fast visualization to shorten procedure time; (2) less recurrence for optimal patient outcomes; (3) lower healthcare utilization costs and lower capital equipment costs; (4) flexibility; and/or (5) fluoroless implementation; or the like. To achieve fast visualization, the IA or EI ecosystem might implement one or more of the following: identify targets in seconds or minutes, maintain occlusion and contact, and/or titrate dosage to reduce number of ablations (thus shortening procedure time), or the like. To achieve less recurrence, the IA or EI ecosystem might implement one or more of the following: utilize powerful predictive analytics in comparison with existing visualization systems, visualize and personalize to patient-specific anatomy, implement multiple checkpoints during each procedure to ensure best patient outcomes, and/or collect occlusion assessment and lesion tagging data, or the like. To achieve lower costs, the IA or EI ecosystem might implement one or more of the following: avoid using expensive capital equipment and/or utilizing MR or XR, which is more than 70% less costly than existing mapping and visualization systems used in arrhythmia treatment or the like. To achieve flexibility, the IA or EI ecosystem might implement one or more of the following: utilize an open system that uses MR or XR with any energy source and/or implement remote sales operation (to achieve geographic flexibility in hard-to-reach locations), or the like. To achieve fluoroless implementation, the IA or EI ecosystem might implement one or more of the following: avoid radiation exposure and/or achieve high resolution imaging o internal cardiac structures without exposing patients to radiation, or the like. Alternatively, or additionally, the IA or EI ecosystem, as represented by FIG. 1 for example, may achieve one or more of the following features or functionalities: (6) improved therapy delivery accuracy for intended targets for better efficacy; (7) reduction in adjacent structure damage; (8) reduced cognitive load for the healthcare professional; (9) reduced exposure to radiation for the patient and/or healthcare professional; (10) simulated patient dye for target organs or tissue; (11) reduction in the number of people needed due to increased control by the user or operator; (12) improved telementoring; (13) improved telemedicine; and/or (14) enables social distancing or total separation (to address pandemic-related issues, such as COVID-19 issues, or the like).

To implement the IA or EI ecosystem, once the anatomy can be visualized and the location of therapy delivery can be navigated to, the choice of device(s) and how to control the device(s) is the next building block. It may be a robotic system like the Hugo/Einstein for soft tissues (Mazor for bone), catheters, delivery systems, surgical tools, etc., such as described above with respect to the one or more devices or equipment 135, or the like. In order for a physician or healthcare professional (such as healthcare professionals 125, or the like) to have real time actionable data, sensors (such as sensors 145, or the like) need to be employed in the system on the patient (e.g., subject 130, or the like), provider, tools, and equipment (e.g., devices or equipment 135, or the like). For example, the visualization tool such as XR hardware (including, but not limited to, Microsoft HoloLens®, or the like) might have several cameras and sensors (not only for visualization) to measure key biometrics in a non-contact manner. In some instances, the visualization tool such as XR hardware may utilize photogrammetry for calibration and/or fiducials (i.e., markers or objects placed in a field of view or imaging system for use as a point of reference or measure, or the like). Depending on the procedure and the need, there may be several sensors that can be employed, for example, eye gazing on the Hugo robot might shut down the system to avoid inadvertent movement or injury, which could be employed via the HoloLens headset on any therapy delivery (including, without limitation, TAVR, TMVR, tumor ablation, cardiac ablation, etc.).

Now that the sensors have gathered the data, the data must be processed for use by the physician or healthcare professional. For instance, a general workflow for processing the data might include the following: (i) problem definition (including, but not limited to, objectives, hypotheses, measurement, cohorts, and/or end points, or the like); (ii) data collection (including, but not limited to, access, transfer, governance, and/or storage of data including, without limitation, internal/external data, historical data, batch data, streaming data, and/or log data, or the like); (iii) data curation (including, but not limited to, quality, cleaning, merging, segmenting, and/or transforming, or the like); (iv) model building (including, but not limited to, features, test models, test analytics, and/or validation, or the like); (v) analysis (including, but not limited to, exploring, analyzing, adjusting, and/or repeating one or more of data mining, AI machine learning or deep learning, statistical analysis, and/or natural language processing, or the like); (vi) visualization (including, but not limited to, graphical, tabular, and/or dashboard visualization of real-time, near-real-time, and/or aggregate data, or the like); (vii) insight and action (including, but not limited to, trends, what, why, and/or how, or the like); and (viii) follow-up (including, but not limited to, prescribing follow-up and long-term monitoring, or the like). Such general workflow may be used to process the three V's of big data—namely, volume (including, without limitation, health records, insurance, transactions, and/or mobile sensors, or the like), velocity (including, without limitation, batch, near-real-time, real-time, and/or streaming, or the like), and variety (including, without limitation, structured, unstructured, semi-structured, and/or the like).

The types of data, sources, and processing methods or analytics might include, but are not limited to, auto-segmentation; geometric analyses; device stabilization and filtering; algorithms; anomalies; outliers; trends over time; image identification or recognition; mobile sensors; measures and prediction for custom, group, etc. (e.g., procedural times, cost, fluoroscopy use, contrast use, team performances, or the like); device acute or chronic performance prediction (e.g. rhythm prediction before and during ablation, or the like); reimbursement or insurance analytics or treatment; health records; transactions; prescriptive modeling; predictive modeling; forecasting or extrapolation; diagnostic or statistical analyses; dashboards or alerts; query or drilldown; Ad hoc reports; standard reports; IoT; data mining; and/or the like. Alternatively, or additionally, the types of data, sources, and processing methods or analytics might include, without limitation, structured; unstructured; semi-structured; multi-device factors; multi-comorbidity factors; data analytics; data privacy; data science; data visualization; simulations; predictions; recommendations; probability of success and adverse events; precise and personalized care; optimizing therapy delivery; evidence based medicine; value-based healthcare ("VBHC"); predictive analytics; prescriptive analytics; care management and real-time patient monitoring; computer aided detection ("CADe"); computer aided diagnosis ("CADx"); medical image processing; device feedback; subject feedback; demographics, global, regional, local, racial, social, familial, diet, mental, emotional, spiritual, attitudinal, genetic, lifestyle, insurance, economic factors, or the like; pre-procedural; intraprocedural; post-procedural; chronic; and/or the like.

In a specific, non-limiting example data use case (i.e., utilizing the HoloLens or the like), goals of a solution architecture for analytics and machine learning might include, but are not limited to: telemetry capture (including, without limitation, 3D positioning of a catheter in real-time, procedure duration and ablation accuracy, heart rhythm, electrical signal reduction, scarred or destroyed tissue, and other vitals, or the like); providing for retrospective analytics (including, without limitation, analyzing individual and arbitrary aggregations of procedures on an ad hoc basis, answering common questions to drive data-driven improvements to procedure (e.g., "how much times is spent in various areas of the heart?" and "what was the accuracy and outcome of the procedure?" or the like)); machine learning integration (including, without limitation, real-time and offline or batch, support proposed use cases (e.g., providing real-time prediction of impact that the procedure has had on electrical signal and prognosis; providing real-time estimate of tissue scarred or destroyed, including percentage considered "in excess"; providing information regarding depth, width, and/or permanency of tissue damage or destruction (e.g., some ablation types like reversible (compared with irreversible) electroporation actually open up cell walls to all for drugs to enter then heal and close up, or the like)); providing real-time anomaly detection of vitals, including dips, peaks, and long-term trend variance; recommending patient-specific ablation locations to reduce probability of repeat surgery; recommending path optimization for procedure based on patient-specific anatomy; or the like)).

With so many data sources, the packaging of display of these into a user interface (such as a UX device, or the like) to only have the right information, at the right time, and in the right place needs to be done to minimize cognitive overload. Although we have shown 3D screen and 3D headset examples, several UX types and feedback loops that can be employed are as described above with respect to UX device 155. All of the parts of the system need to communicate in a seamless manner in order to be useful in real time. The parts of a non-limiting XR or IA/EI ecosystem, according to some embodiments, might include, without limitation, headset; tethered unit; cloud; data warehouse; data lake; computer processor; and/or the like. Lastly, the application of the ecosystem can be deployed on various subjects (as described above with respect to subject 130).

In many aspects, system 100 may provide IA or EI ecosystem functionality for any number of tasks, such as those described in detail in the '278, '283, '289, and '632 Applications (i.e., the "Related Applications"), which have already been incorporated herein by reference in their entirety for all purposes. The various embodiments described herein focus on those tasks associated with CIED placement including, but not limited to, at least one of a cardiac mapping procedure, a cardiac resynchronization therapy ("CRT") device installation procedure, a right ventricular pacing ("RVP") procedure, a His bundle pacing ("HBP") procedure, a left bundle branch pacing ("LBBP") lead placement procedure, a right bundle branch pacing ("RBBP") lead placement procedure, a bilateral bundle branch area pacing "(BBBP") lead placement procedure, an implant procedure, an implantable cardioverter defibrillator ("ICD") device installation procedure, an extravascular ICD ("EV-ICD") device installation procedure, a pacemaker installation procedure, a miniature leadless implant installation procedure, or a remote monitoring device installation procedure, and/or the like.

In such operations, system hub or computing system 105a or 105b (collectively, "computing system" or the like) might receive one or more first layer input data from one or more first devices, the one or more first layer input data comprising at least one of movement data, position data, relative distance data, or externally observable data for each of one or more persons (e.g., subject 130, healthcare professional(s) 125, etc.) and one or more objects (e.g., device(s) or equipment 135, furniture, etc.) within a room (i.e., clinical environment 170, or the like). In such cases, the one or more first devices may include at least one of imaging system(s) 140, sensor(s) 145, and/or the like, that are configured to obtain, capture, or otherwise provide the one or more first layer input data. The computing system might receive one or more second layer input data from one or more second devices, the one or more second layer input data comprising at least one of one or more patient sensor data for monitoring procedure-relevant aspects of a patient (i.e., subject 130), one or more patient imaging data for monitoring images of one or more portions of a body of the patient, or one or more navigation and mapping data for monitoring one or more surgical devices (i.e., the devices or equipment 135, or the like) relative to the one or more portions of the body of the patient, and/or the like. In such cases, the one or more second devices may include at least one of device(s) or equipment 135, imaging system(s) 140, sensor(s) 145, and/ or the like, that are configured to obtain, capture, or otherwise provide the one or more second layer input data.

The computing system might analyze the received one or more first layer input data and the received one or more second layer input. The computing system might generate one or more recommendations for guiding a medical professional (i.e., healthcare professional(s) 125, or the like) in performing a cardiac implantable electronic device ("CIED") placement procedure in a heart of the patient, based at least in part on the analysis, the generated one or more recommendations comprising 3D or 4D mapped guides toward, in, and around the heart of the patient. The computing system might then generate one or more XR images (or one or more XR experiences), based at least in part on the generated one or more recommendations, and might present the generated one or more XR images (or one or more XR experiences) using a UX device 155. According to some embodiments, the one or more XR images might be dynamic images, which might include an overlay of data models depicting at least one of electrical pulses, blood flow, tissue movement, damage, stress, and/or the like, and thus may not be a still frame in 3D. In some embodiments, the one or more XR images might include, without limitation, at least one of one or more AR images, one or more AR videos, one or more VR images, one or more VR videos, one or more MR images, one or more MR videos, one or more XR images, or one or more XR videos, and/or the like.

According to some embodiments, the generated one or more XR images might be presented to provide one or more of: a guide for a medical professional (e.g., healthcare professional(s) 125, or the like), a navigation tool during the CIED placement procedure, a proximity detection tool during the CIED placement procedure, a 3D or 4D visualization view of the at least one or more portions of the patient, a heads-up display of at least one of the one or more first layer input data, a heads-up display of at least one of the one or more patient sensor data, a heads-up display of at least one of the one or more patient imaging data, a heads-up display of physiological data of the patient, or a heads-up display of procedure-related data of the patient, and/or the like. In some instances, generating the one or more XR images might comprise combining or mapping the received one or more first layer input data and the received one or more second layer input into a combined 3D or 4D representation, based at least in part on the analysis and the generated one or more recommendations; and generating the one or more XR images based on the combined 3D or 4D representation.

In some embodiments, the computing system might track the one or more surgical devices (e.g., devices or equipment 135, or the like), using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

According to some embodiments, the computing system might receive one or more control inputs from the medical professional; might analyze the received one or more control inputs in conjunction with analysis of the received one or more first layer input data and the received one or more second layer input data; might generate one or more control instructions based at least in part on the analysis, the generated one or more control instructions taking into account movement including at least one of movement of the heart and surrounding tissue due to continual beating of the heart and due to one or more of table movement, fluid loss, respiration of the patient, or movement or shifting of at least one portion of the body of the patient; and might send the generated one or more control instructions to a robotic system (which may, in some cases, be included among the device(s) or equipment 135, or more specifically among the surgical tool(s) or device(s) 135a, or the like) to cause the robotic system to implement CIED placement within the heart of the patient as part of the CIED placement procedure.

In some instances, at least the processes of receiving the one or more first layer input data, the one or more second layer input data, analyzing the received one or more first layer input data and the received one or more second layer input, generating the one or more recommendations, generating the one or more XR images, presenting the generated one or more XR images, receiving the one or more control inputs, analyzing the received one or more control inputs, generating the one or more control instructions, and/or sending the generated one or more control instructions may occur in a manner that is at least one of continual, dynamic, feedback-looped, updated, in real-time, or in near-real-time, and/or the like, during the course of the CIED placement procedure.

In some embodiments, the received one or more control inputs may comprise hand-movement-based control inputs resulting from movement of one or more hands of the medical professional. In such cases, analyzing the received one or more control inputs may comprise determining whether the hand-movement-based control inputs comprise inputs indicative of excessive movement of at least one hand of the one or more hands of the medical professional. As such, generating the one or more control instructions may comprise, based on a determination that the hand-movement-based control inputs comprise inputs indicative of excessive movement of at least one hand of the medical professional, the computing system generating one or more compensated control instructions that include control instructions that are based on hand-movement-based control inputs while dampening one or more particular control inputs that are based on excessive movement of the at least one hand of the medical professional. In some cases, using robotic placement, movement, and/or collision detection, the excessive movement of the at least one hand of the medical professional may be tracked relative to the robotic arm or relative to an implant device or catheter, with the computing system generating the one or more compensated control instructions accordingly.

According to some embodiments, the data processing and computation may be performed locally (e.g., at system hub/computing system 105a, mapping and navigation system 115a, XR platform/system 150, and/or data analytics/AI system 160a, or the like), may be performed at a remote system(s) (e.g., at system hub/computing system 105b, mapping and navigation system 115b, data analytics/AI system 160*b*, another server(s), and/or a cloud computing-based system, or the like), or may be performed using a combination of local and/or remote systems, or the like.

In some aspects, the IA or EI ecosystem may utilize AI-assisted image processing for determining an appropriate target site, image- and/or sensor-based CIED deployment by a robotic machine, near-instant signal processing to confirm the success of the CIED deployment, ensuring complete connection to the CIED, ensuring complete and/or customized device programming of the CIED based on the patient's indication (e.g., pathological condition as monitored by the IA or EI ecosystem), confirming CIED location (e.g., location of pacing lead, or the like), and collecting results of the signal processing (and/or of the CIED), and/or the like, all performed autonomously (or with minimal if any human input). In some embodiments, the procedure may be performed without fluoroscopy.

These and other functions of the system 100 (and its components) are described in greater detail below with respect to FIGS. 2-7.

Figure 2:
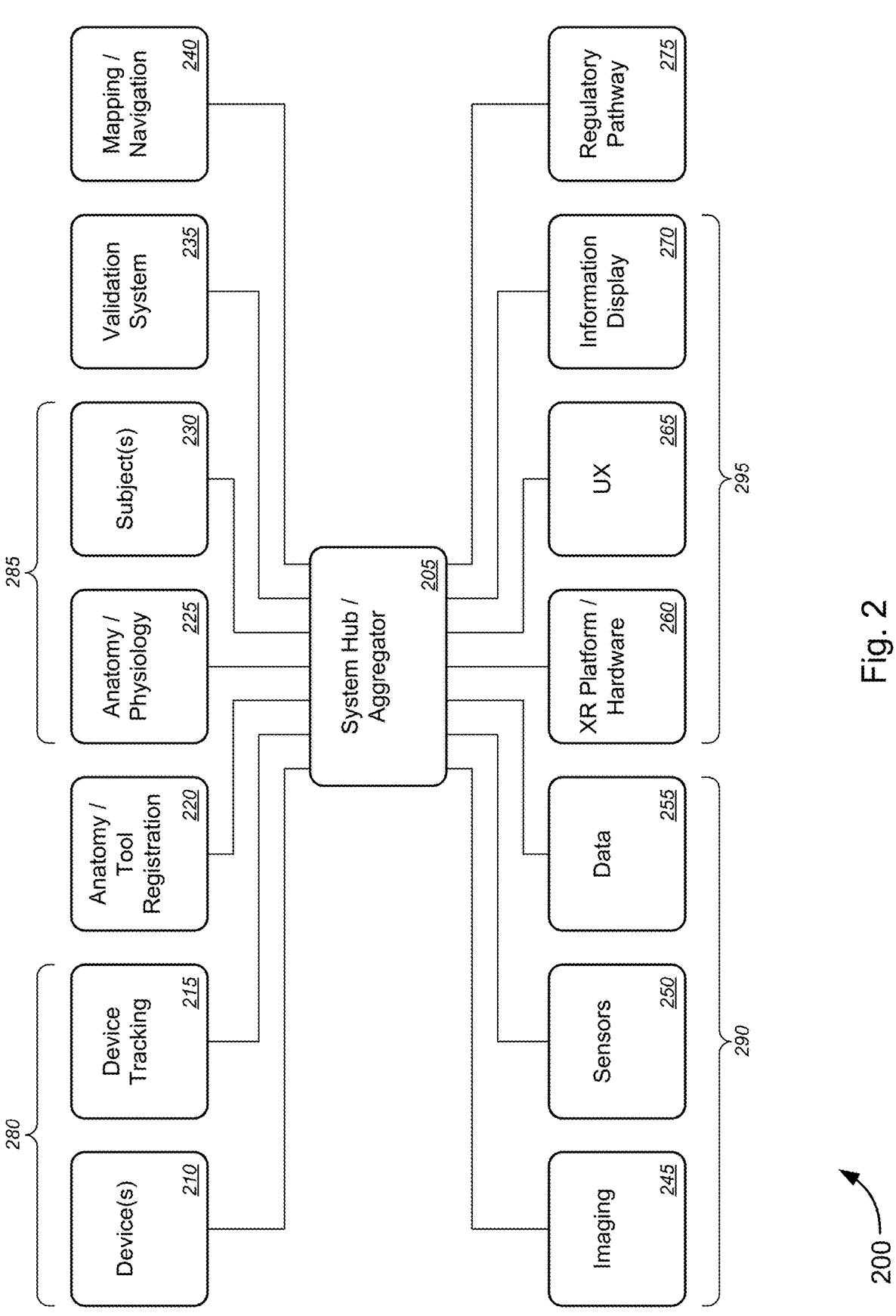
FIG. 2 is a schematic diagram illustrating a non-limiting example of building blocks for an IA or EI ecosystem that may be implemented for CIED placement procedures, in accordance with various embodiments.

FIG. 2 is a schematic diagram illustrating a non-limiting example 200 of building blocks for an IA or EI ecosystem that may be implemented for CIED placement procedures, in accordance with various embodiments.

With reference to the non-limiting example 200 of FIG. 2, the IA or EI ecosystem 200 might comprise a system hub or aggregator (block 205) and a plurality of components or building blocks of the IA or EI ecosystem (blocks 210-275) that are communicatively coupled with the system hub or aggregator (at block 205). In some embodiments, the plurality of components might include, without limitation, at least one of one or more devices (block 210) configured to perform one or more tasks (such as performing one or more medical procedures, including, but not limited to, a cardiac implantable electronic device ("CIED") placement procedure, or the like), a device tracking system (block 215) configured to track each device, an anatomy and/or tool registration system (block 220) configured to register anatomy of a subject and/or tools used, anatomy or physiology (block 225) (i.e., anatomy or physiology of subjects or patients, or the like), one or more subjects or patients (block 230), a validation system (block 235) configured to validate information, a mapping or navigation system (block 240), one or more imaging systems (block 245), one or more sensors (block 250), data (particularly, regarding the one or more devices and/or the device tracking, or the like) (block 255), extended reality ("XR") platform or hardware (block 260), user experience ("UX") device or system (block 265), information display (block 270), or regulatory pathway system (block 275), and/or the like. The blocks 210 and 215 corresponding to the one or more devices and the device tracking system, respectively, are directed to or focused on the device or instrument aspects 280 of the system, while the blocks 225 and 230 corresponding to the anatomy or physiology and the one or more subjects, respectively, are directed to or focused on aspects of the subject(s) or patient(s) 285. Likewise, the blocks 245-255 corresponding to the one or more imaging systems, the one or more sensors, and the data, respectively, are directed to or focused on the data collection aspects 290 of the system, while the blocks 260-270 corresponding to the XR hardware, the UX device or system, and the information display, respectively, are directed to or focused on the user interface aspects 295.

According to some embodiments, the one or more devices (at block 210) may correspond to (or may include) the one or more devices or equipment 135 of system 100 of FIG. 1, or the like.

In some embodiments, the mapping or navigation system (at block 240) might include, without limitation, at least one of an XR computing system, a medical procedure computing system, a hub computing system, a three-dimensional ("3D") graphical processing unit, a cluster computing system, a four-dimensional ("4D") graphics computing system, a server computer, a cloud computing system, or a distributed computing system, and/or the like.

According to some embodiments, the one or more imaging systems (at block 245) may correspond to (or may include) the one or more imaging devices or systems 140 of system 100 of FIG. 1, or the like.

In some embodiments, the one or more sensors (at block 250) may correspond to (or may include) the one or more sensors 145 of system 100 of FIG. 1, or the like.

According to some embodiments, the user interface aspects 295 (at blocks 260-270) might include, but not limited to, at least one of a headset, UX glasses, a viewing window, a supplement to existing glasses, headphones, UX contact lenses, a heads-up display ("HUD") device, a 3D spatial sound system, a telemonitoring system, a rigid robotic device control and sensory feedback system, a soft robotic device control and sensory feedback system, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a 3D printed reconstruction system, a customized view generation system, a ghosting and prediction system, a master-slave control system, an annotation system, or a haptic feedback system, and/or the like.

Figure 3:
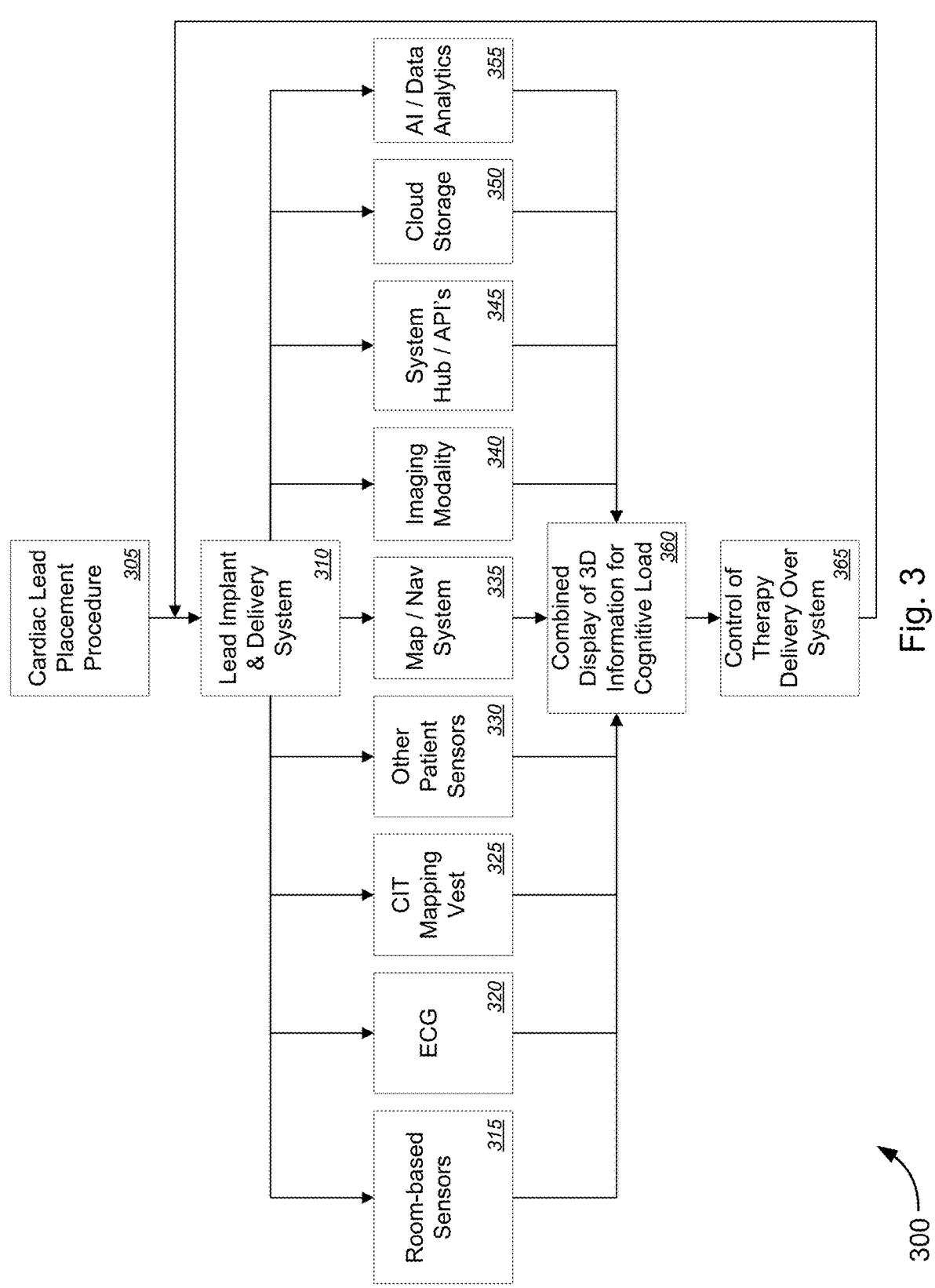
FIG. 3 is a schematic diagram illustrating a non-limiting example of a process stack for implementing an IA or EI ecosystem for CIED placement procedures, in accordance with various embodiments.

FIG. 3 is a schematic diagram illustrating a non-limiting example 300 of a process stack for implementing an IA or EI ecosystem for CIED placement procedures, in accordance with various embodiments.

With reference to the non-limiting example 300 of FIG. 3, a general process stack for implementing an IA or EI ecosystem for a cardiac implantable electronic device ("CIED") placement procedure, which may include, but is not limited to, at least one of a cardiac resynchronization therapy ("CRT") procedure, a right ventricular pacing ("RVP") procedure, a His bundle pacing ("HBP") procedure, a left bundle branch pacing ("LBBP") lead placement procedure, a right bundle branch pacing ("RBBP") lead placement procedure, a bilateral bundle branch area pacing "(BBBP") lead placement procedure, an implantable cardioverter defibrillator ("ICD") device installation procedure, an extravascular ICD ("EV-ICD") device installation procedure, or a miniature leadless implant installation procedure, and/or the like. Such a process stack may begin with a selection of a CIED placement procedure or operation (at block 305). In response to such selection, a lead implant and delivery system may be implemented (at block 310). The IA or EI ecosystem might utilize, in conjunction with the lead implant and delivery system (with sensors on the therapy delivering device also being referred to as "contacting internal sensors" or the like), a number of devices or equipment, sensors, imaging systems, and other systems (collectively, "lead implant and delivery sub-systems" or the like), including, but not limited to, at least one of one or more room-based sensors (also referred to as "contactless sensors" or the like) (at block 315), an electrocardiogram ("ECG") monitor (at block 320), a mapping vest (e.g., CardioInsight™ ("CIT") mapping vest, or the like; also referred to as "contacting external sensors" or the like) (at block 325), other patient sensors (at block 330), a mapping and/or navigation system (at block 335), imaging modality (at block 340), a system hub and/or application programming interfaces ("API's") (at block 345), cloud storage (at block 350), or artificial intelligence ("AI") and/or data analytics (at block 355), and/or the like. In some cases, the mapping vest CardioInsight™ ("CIT") mapping vest, or the like, may be a single-use, disposable, multi-electrode vest that gathers cardiac electrophysiological data from the surface of the patient's body, with such data being combined with imaging data taken of the patient to produce and display simultaneous, bi-atrial and bi-ventricular 3D cardiac maps, or the like. Data from these sub-systems may be combined to generate a combined display of three-dimensional ("3D") information or four-dimensional ("4D") information (i.e., three-dimensional ("3D") information plus at least one of real-time updates, dynamic modeling, or data streaming, and/or the like) for cognitive load (at block 360). Such 3D or 4D information may be used to control therapy delivery over the system (e.g., via use of robotic systems, robotic arms, or the like) (at block 365). The process at blocks 310-365 may be repeated as necessary or as desired.

Figure 4B:
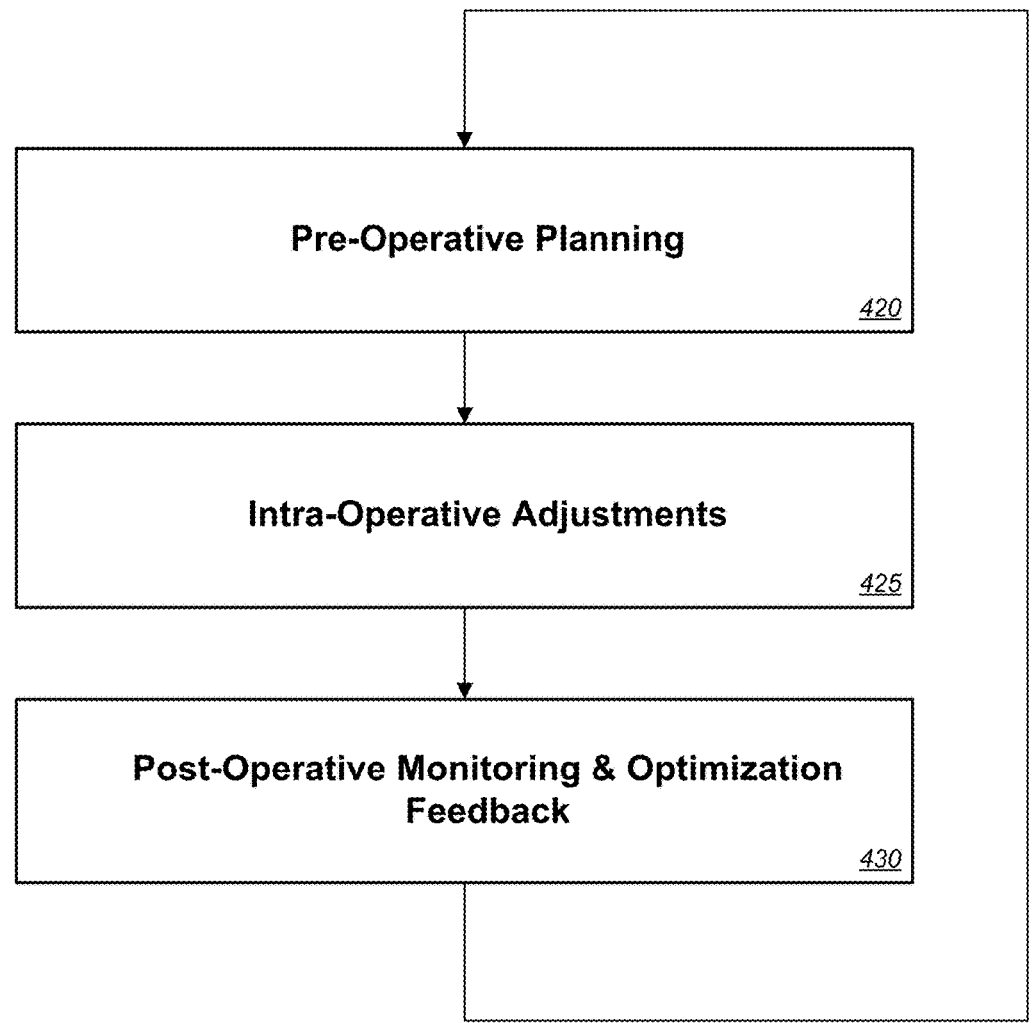
FIG. 4B is a flow diagram illustrating a non-limiting example of interactions among "pre-operative planning," "intra-operative adjustments," and "post-operative monitoring" with an optimization feedback loop, in accordance with various embodiments.

FIG. 4A is a flow diagram illustrating a non-limiting example 400 of feedbacked interactions among three sub-layers of imbedded and contactless sensors, data, and vision systems that may be used as part of an IA or EI ecosystem implementation for CIED placement procedures, in accordance with various embodiments. FIG. 4B is a flow diagram illustrating a non-limiting example 400' of interactions among "pre-operative planning," "intra-operative adjustments," and "post-operative monitoring" with an optimization feedback loop, in accordance with various embodiments.

With reference to the non-limiting example 400 of FIG. 4A, the IA or EI ecosystem for implementing CIED placement procedures may employ three sub-layers of imbedded and contactless sensors, data, and vision systems working together in a feedback loop, the three sub-layers including, without limitation: (1) Top Sub-Layer (or Planning Layer) 405, (2) Intermediate Sub-Layer (or Decision Layer) 410, and (3) Base Sub-Layer (or Action Layer or Execution Layer) 415. These various sub-layers feedback on each other (as depicted in FIG. 4A by the arrows connecting one sub-layer to another and back again).

According to some embodiments, the Top Sub-Layer (Planning Layer) 405 represents a high level layer that captures the entire room including large movements of the patient, medical staff, and medical equipment such as the robotic linkages and delivery system. This can be done by multiple techniques together or separately, including, but not limited to, infrared and photogrammetry techniques. For example, one or more depth cameras (e.g., Kinect™ depth cameras, or the like) may be used to map the entire room, to track distances between users, to track distances between robotic linkages, and to track position(s), orientations(s), and/or movement(s) of the patient. Algorithms with known degrees of freedom of each of these can determine the range of motion, and machine learning simulations can recommend a location(s) of each in real-time or near-real-time. This can then be displayed on the Intermediate Layer 410 for the user(s) or medical professional(s) to take action via the Base Layer 415.

Information and/or outcomes facilitated by the Top Sub-Layer 405 may include, without limitation, (a) equipment and/or robotic system setup monitoring and suggestions to the next layer (which may aid in robot and human collision predictions and warnings, or the like); (b) staff location and workflow monitoring (including ensuring social distancing protocols are met, or the like); (c) obtaining or generating port (or surgical device placement) locations, setup, monitoring, and/or suggestions, or the like; (d) monitoring patient posture, respiration, shifting positions, or the like; (e) monitoring biometrics of patient and/or staff (including, but not limited to, temperature, heart rate, oxygen level, etc.); (f) monitoring staff safety via vision tracking or the like (in some cases, via facial recognition AI techniques) to ensure safety protocols are met (including, but not limited to, proper face mask wearing, sterile fields, identification of all equipment and disposables, etc.); (g) tracking cell operating system ("COS") layouts and traffic flow (i.e., using spatial mapping, or the like); (h) producing workflows for equipment and staff (in some cases, displayed in heat maps and pathways, or the like); (i) automating documentation while blurring out or redacting private areas of text and facial features, or the like; and/or the like.

In some embodiments, the Intermediate Sub-Layer (Decision Layer) 410 represents decision-making tools that provide the interface and feedback loop(s) between the user(s) or medical professional(s), the equipment, and the devices. For example, this layer may be used to gather non-contact sensor data from the Top Sub-Layer 405 and tool and/or patient data from the Base Sub-Layer 415, then to analyze, recommend, and display for the user(s) or medical professional(s) to make an Extended Intelligent ("EI") decision(s). These recommendations can come with displayed boundaries and/or guides, probability of success, recommended similar cases/approaches/outcomes for reference, etc. This will allow the user(s) or medical professional(s) to interact with a virtual mockup of the system, to move around components of the system, to compare options to optimize, and/or to verify placement once moved, and/or the like.

Features of the Intermediate Sub-Layer may include, without limitation, (a) visualizing and integrating 3D anatomical structures and electroanatomic mapping ("EAM") data in near-real-time (i.e., in 4D) at this level in many ways, including, but not limited to, via a mapping vest (e.g., CardioInsight™ ("CIT") mapping vest, or the like) or via electromechanical wave imaging ("EWI") ultrasound, or the like; (b) enabling equipment setup, including virtual overlays of base and articulating sections; (c) providing remote assistance, tele-mentoring, and tele-surgery via display (where the display and control may be through multiple modalities, including, but not limited to, headsets, laptops, phones, tablets, command center, etc.); (d) utilizing imbedded sensors—including, but not limited to, microelectromechanical system ("MEMS")-based sensors, vibration sensors, rotation sensors, acceleration sensors, temperature sensors, etc.—to provide immediate feedback loop(s) for highlighting and/or addressing concerns such as robotic arm and/or human collisions, or for otherwise aiding in validating non-contact sensing, or the like; (e) integrating XR analytics data sources and machine learning including security and privacy (e.g., blurring out faces of patients, physicians, staff, etc., using facial recognition techniques; blurring out or redacting personal, patient or healthcare-related data, etc., in written documents using object recognition techniques; and/or the like); and/or the like. In some cases, machine learning methods for visual tracking, human pose estimation, human-object interaction models, tool tracking, estimate durations of activities, suggested tool types, procedure techniques, recovery planning, and change-over for next procedure(s) may include, but are not limited to, (i) predictive movements from Convolutional Neural Network and Fully Connected Networks, or the like; and/or (ii) Sequential decision-making such as Markov Decision Process ("MDP"), or the like.

According to some embodiments, the Base Sub-Layer (Action Layer) 415 represents medical tools interfacing with the patient to apply therapy. The three sub-layers may have overlapping functions and can calibrate and/or validate each other throughout the procedure.

Some features of the Base Sub-Layer may include, without limitation, (a) providing navigation and mapping of surgical devices, using optical-based, RFID-based, electromagnetic-based, impedance-based, Bluetooth™-based, RF-based, and/or ultrasound-based navigation and mapping functionalities; (b) enabling a shared session across multiple locations that may be employed by multiple devices and/or platforms; (c) enabling virtual and/or augmented reality display at procedure location or at a separate location for tele-mentoring and/or tele-surgical control (i.e., where interaction with the virtual display can physically control the surgical device(s)), and, in some cases, utilizing haptic feedback within the control center and/or gloves of the user(s) or medical professional(s) to achieve more realistic feedback loop(s) and optimal outcome(s); (d) utilizing multiple modalities for device tracking, with near-real-time recommendations of therapy target being displayed in augmented reality via feedback loop of the system, where the feedback loop may be used to predict and track catheter trajectories, angles, distance to target, etc. In some instances, other features that may be displayed for better decision-making may include, but are not limited to, (i) displaying how electrical system breaks out into branches; (ii) displaying spearing and/or capturing of left and right bundle branches, rings of circuitry, etc.; (iii) displaying in 3D both predicted trajectories (whether based on predictions via AI or based on annotations of the user's or medical professional's own pathway) and tracked (or actual) trajectory; and/or the like.

Referring to the non-limiting example 400' of FIG. 4B, the IA or EI ecosystem for implementing CIED placement procedures may additionally employ the following three stages: (1) a Pre-Operative Planning Stage 420; (2) an Intra-Operative Adjustments Stage 425; and (3) a Post-Operative Monitoring and Optimization Feedback Stage 430. The process may start at the Pre-Operative Planning Stage 420, then proceed to the Intra-Operative Adjustments Stage 425, subsequently proceed to the Post-Operative Monitoring and Optimization Feedback Stage 430, and loop back (as necessary) to the Pre-Operative Planning Stage 420, with the cycle looping as many times as required or as desired to ensure continued optimization of the CIED placement procedures.

At the Pre-Operative Planning Stage 420, the IA or EI ecosystem may collect sensor data from one or more sensors (e.g., imaging system(s) 140, 245, and 340, sensor(s) 145, 250, and 315-340, etc. of FIGS. 1-3, or the like, which are discussed in detail above). In some cases, the IA or EI ecosystem may perform at least one of the functions of the Top Sub-Layer (Planning Layer) 405 as well as at least one of the functions of the Intermediate Sub-Layer (Decision Layer) 410, as discussed above with respect to FIG. 4A. The CIED placement procedure, as discussed herein, may then be performed based on sensor data, recommendations, and physician plans obtained or arising from the Pre-Operative Planning Stage 420.

During the procedure itself, at the Intra-Operative Adjustments Stage 425, the IA and EI ecosystem may continue to collect sensor data from the one or more sensors, and may perform at least one of the functions of the Base Sub-Layer (Action or Execution Layer) 415 as well as at least one of the functions of the Intermediate Sub-Layer (Decision Layer) 410, as discussed above with respect to FIG. 4A. Adjustments to the delivery of the CIED placement may be implemented in real-time based any updates or changes to the sensor data and recommendations obtained during the Intra-Operative Adjustments Stage 425.

Following a predetermined time period after the CIED placement procedure (e.g., 30 days, 60 days, and/or 90 days, or the like), the Post-Operative Monitoring and Optimization Feedback Stage 430 may be performed. At the Post-Operative Monitoring and Optimization Feedback Stage 430, the IA and EI ecosystem may collect sensor data from the one or more sensors, and may once again perform the at least one of the functions of the Top Sub-Layer (Planning Layer) 405 as well as the at least one of the functions of the Intermediate Sub-Layer (Decision Layer) 410, as discussed above with respect to FIG. 4A. In some cases, the IA and EI ecosystem may perform a different set or combination of functions of each of the Top Sub-Layer (Planning Layer) 405 and/or the Intermediate Sub-Layer (Decision Layer) 410. The IA and EI ecosystem may determine based on the sensor data and recommendations obtained or arising from the Post-Operative Monitoring and Optimization Feedback Stage 430 whether there has been a change or a difference in the sensor data, and, if so, whether the change or difference is indicative of a positive change (e.g., an expected, successful placement of the CIED, resulting in good results being obtained from the CIED, without adverse signs of stress or injury in the patient's body, or the like) or a negative change (e.g., where an issue arises from one or more of improper placement of the CIED, results not being properly obtained from the CIED, and/or adverse signs of stress or injury in the patient's body are observed, or the like). The operations of the Post-Operative Monitoring and Optimization Feedback Stage 430 may be performed repeatedly over a predetermined period (e.g., every day for a week, or the like), which may also be repeated the following one or more months. Based on the sensor data results and recommendations obtained during the Post-Operative Monitoring and Optimization Feedback Stage 430, the process may loop back to the Pre-Operative Planning Stage 420, the Intra-Operative Adjustments Stage 425, and the Post-Operative Monitoring and Optimization Feedback Stage 430 during a follow-on CIED placement procedure (or correction procedure), or the like.

Figures 5A, 5B, 5C:
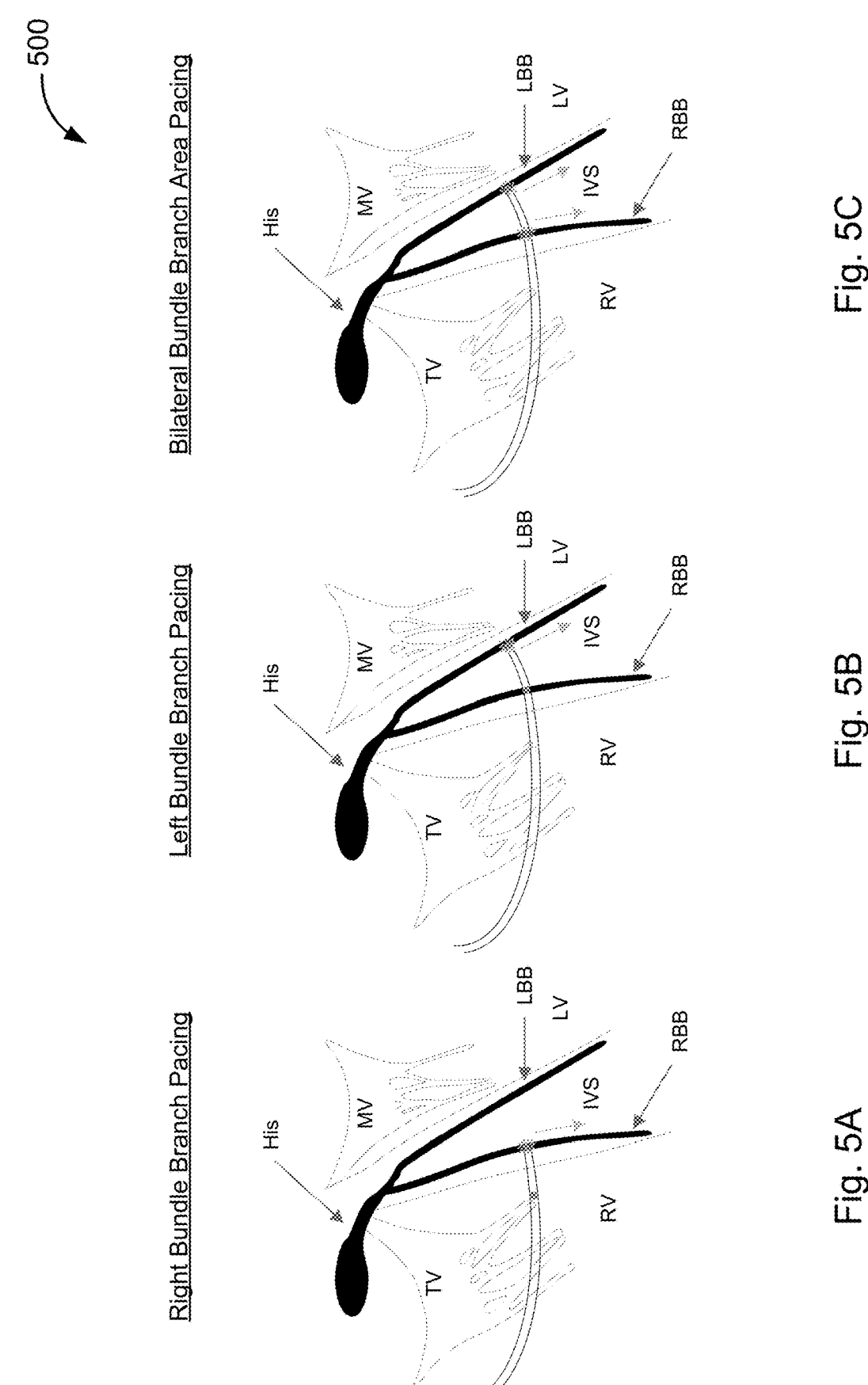
FIGS. 5A-5C are schematic diagrams respectively illustrating His-Purkinje system pacing such as right bundle branch pacing ("RBBP"), left bundle branch pacing ("LBBP"), and bilateral bundle branch area pacing ("BBBP") that represent some non-limiting examples of the CIED placement procedures that may be performed using an IA or EI ecosystem implementation, in accordance with various embodiments.
Figure 5D:
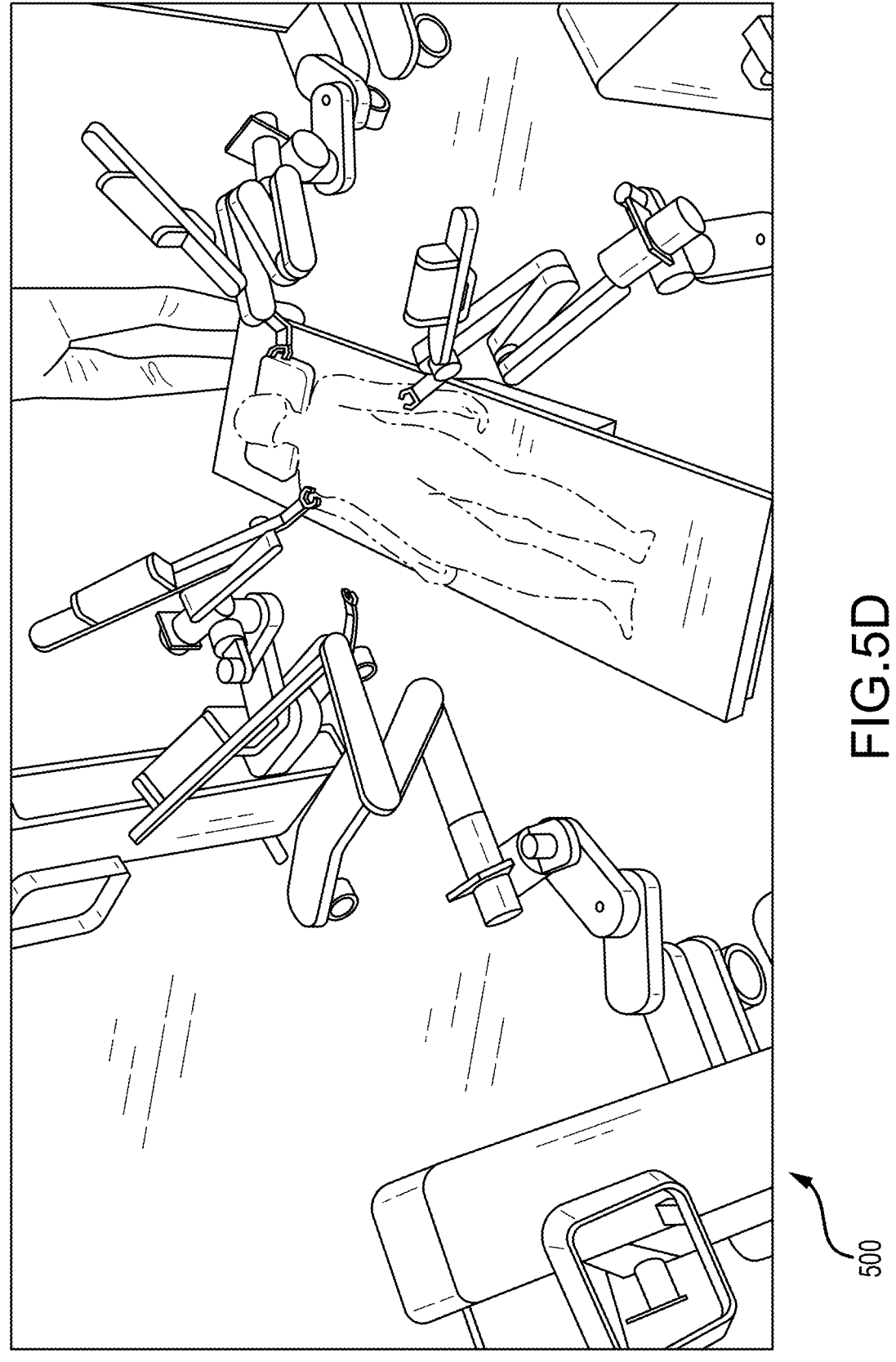
FIGS. 5D and 5E are diagrams illustrating non-limiting examples of images that may be presented on a two-dimensional display and a three-dimensional display, respectively, as part of a display output for an IA or EI ecosystem implementation for CIED placement procedures, in accordance with various embodiments.
Figure 5E:
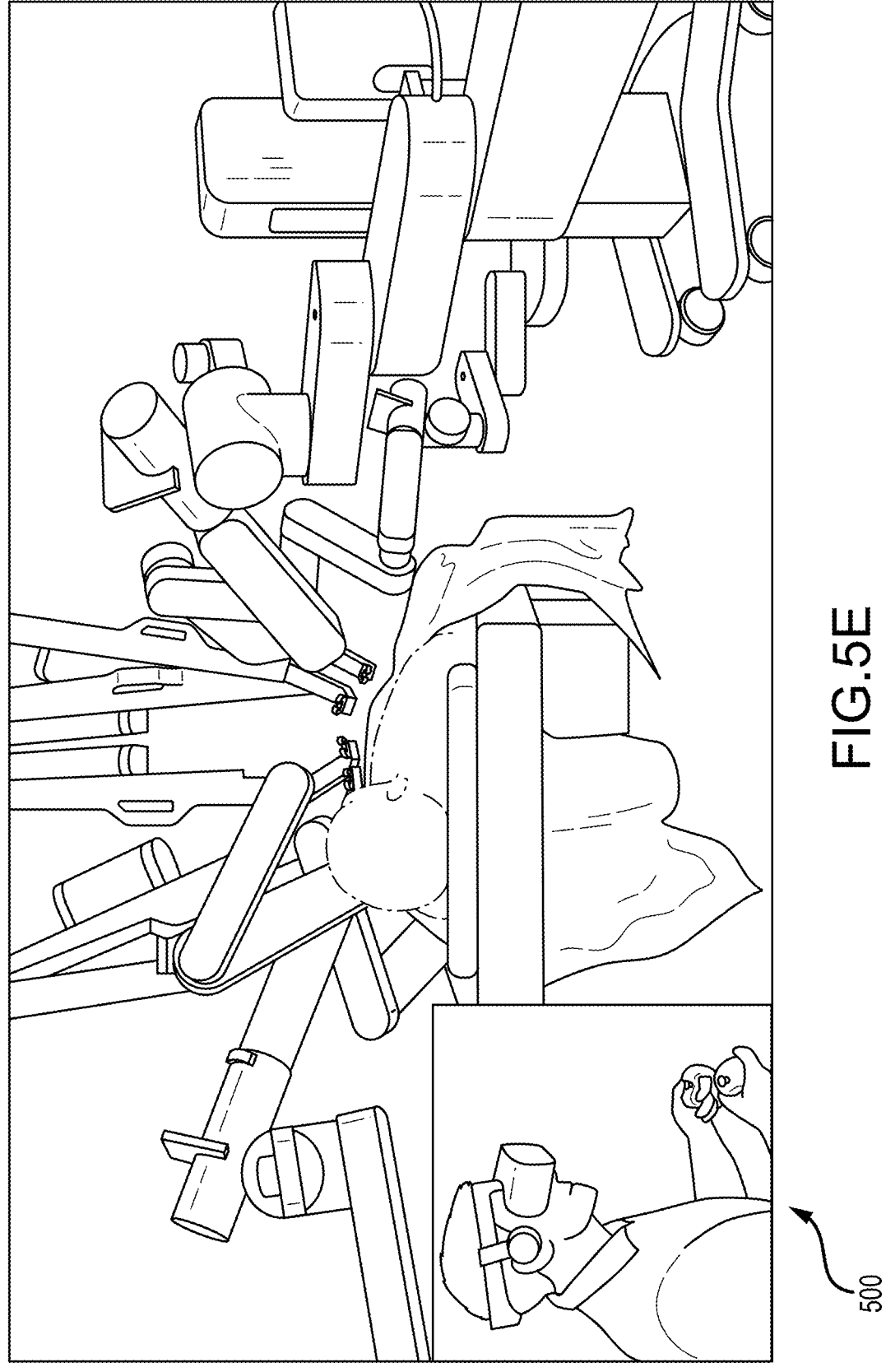

FIGS. 5A-5E (collectively, "FIG. 5") illustrate various non-limiting examples 500 of IA or EI ecosystem implementations for CIED placement procedures, in accordance with various embodiments. FIGS. 5A-5C are schematic diagrams respectively illustrating His-Purkinje system pacing such as right bundle branch pacing ("RBBP"), left bundle branch pacing ("LBBP"), and bilateral bundle branch area pacing ("BBBP") that represent some non-limiting examples of the CIED placement procedures that may be performed using an IA or EI ecosystem implementation, in accordance with various embodiments. FIGS. 5D and 5E are diagrams illustrating non-limiting examples of images that may be presented on a two-dimensional ("2D") display and a three-dimensional ("3D") display, respectively, as part of a display output for an IA or EI ecosystem implementation for CIED placement procedures, in accordance with various embodiments.

With reference to FIGS. 5A-5C, the His bundle, the left bundle branch ("LBB"), and the right bundle branch ("RBB") are depicted in relation to the tricuspid valve ("TV") and the mitral valve ("MV") as well as in relation to the left ventricle ("LV"), the right ventricle ("RV"), and the interventricular septum ("IVS"). As shown in FIG. 5A, when a CIED (e.g., a pacing lead helix, or the like; depicted by the dark gray circle) is placed at the RBB, electrocardiogram ("ECG") and intracardiac electrogram ("EGM") data (represented in FIG. 5A by light-gray rays surround the dark gray circle denoting the CIED and by the light-gray arrow pointing downward along the IVS) associated with the RBB may be monitored during intrinsic rhythm and pacing. As shown in FIG. 5B, when the CIED (e.g., a pacing lead helix, or the like; depicted by the dark gray circle) is placed at the LBB, ECG and intracardiac EGM data (represented in FIG. 5B by light-gray rays surround the dark gray circle denoting the CIED and by the light-gray arrow pointing downward along the IVS) associated with the LBB may be monitored during intrinsic rhythm and pacing. In a similar manner, as shown in FIG. 5C, when two CIEDs (depicted by the dark gray circles) are placed at both the RBB and the LBB (referred to as bilateral bundle branch area pacing ("BBBP"), which is conventionally difficult to achieve with conventional imaging and sensory systems, but more easily achievable using the IA or EI ecosystem described herein), ECG and intracardiac EGM data (represented in FIG. 5C by light-gray rays surround each of the two dark gray circles denoting the two CIEDs and by the corresponding two light-gray arrows pointing downward along the IVS) associated with both the RBB and the LBB may be monitored during intrinsic rhythm and pacing.

Turning to FIGS. 5D and 5E, the IA or EI ecosystem provides or presents a user or medical professional with XR images (as described in detail above with respect to the embodiments of FIGS. 1-4, or the like), and may be displayed as a 2D display (e.g., on a laptop, monitor, or other screen display/projection, or the like) (as shown in FIG. 5D) or as a 3D display (e.g., via VR, AR, MR, and/or XR devices (e.g., UX devices), or the like) (as shown in FIG. 5E). Although FIGS. 5D and 5E depict the room-view, the various embodiments are not so limited, and the IA or EI ecosystem may provide or present the user or medical professional with XR-image-based overlays, cutouts, or other 2D, 3D, and/or 4D representations of the heart, targeted portions of the heart, trajectories, and planned outlines of the CIED placement procedure, so as to enable the user or medical professional to more easily and accurately achieve BBBP CIED placement, or any other cardiac (or non-cardiac) medical procedures, or the like.

Figure 6A:
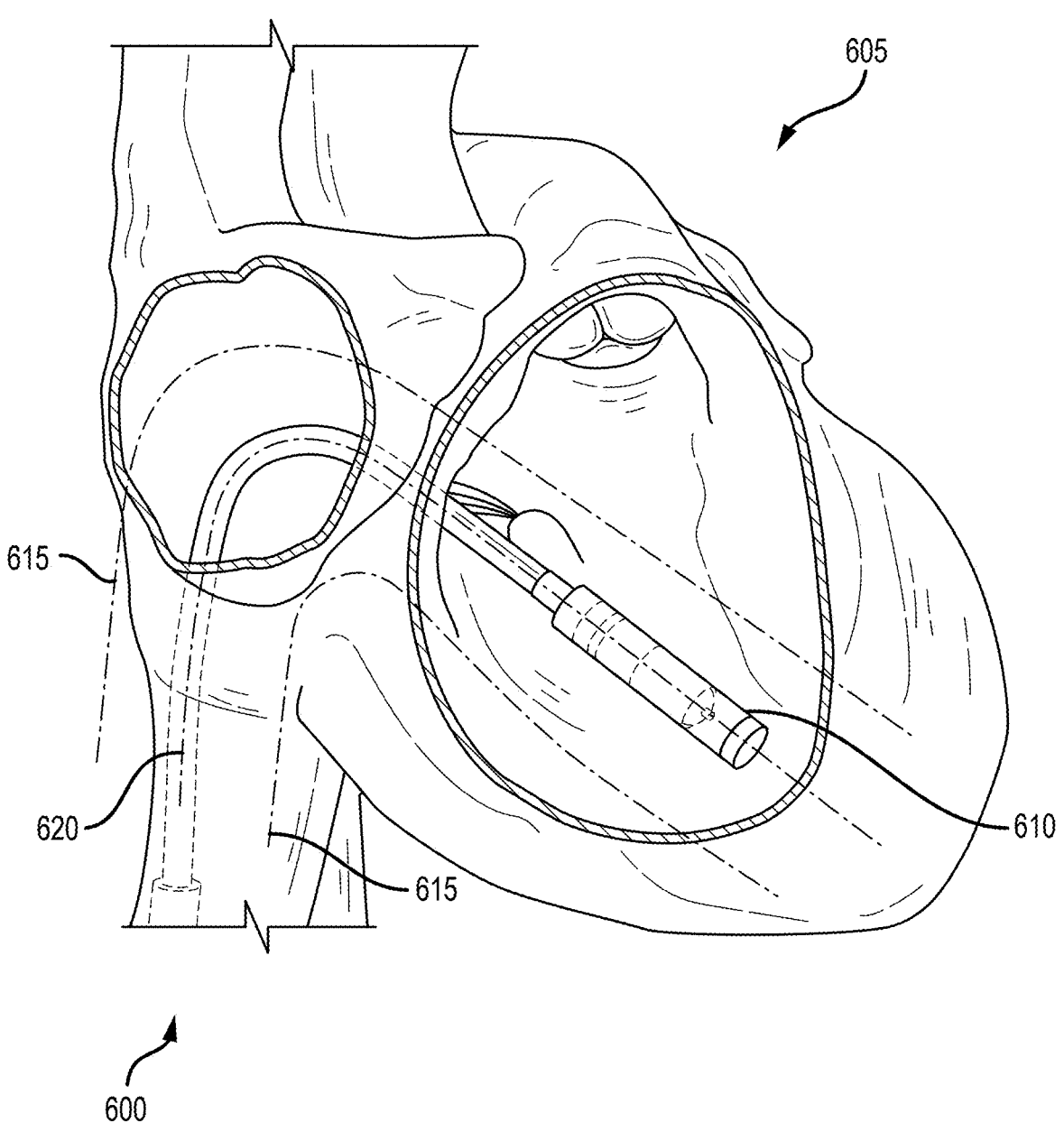
FIGS. 6A and 6B are diagrams illustrating non-limiting examples of images that may be presented as part of a display output for an IA or EI ecosystem implementation for CIED placement procedures such as leadless implant procedures, cardiac sense/stimulation electrode placement procedures, or the like, in accordance with various embodiments.
Figure 6B:
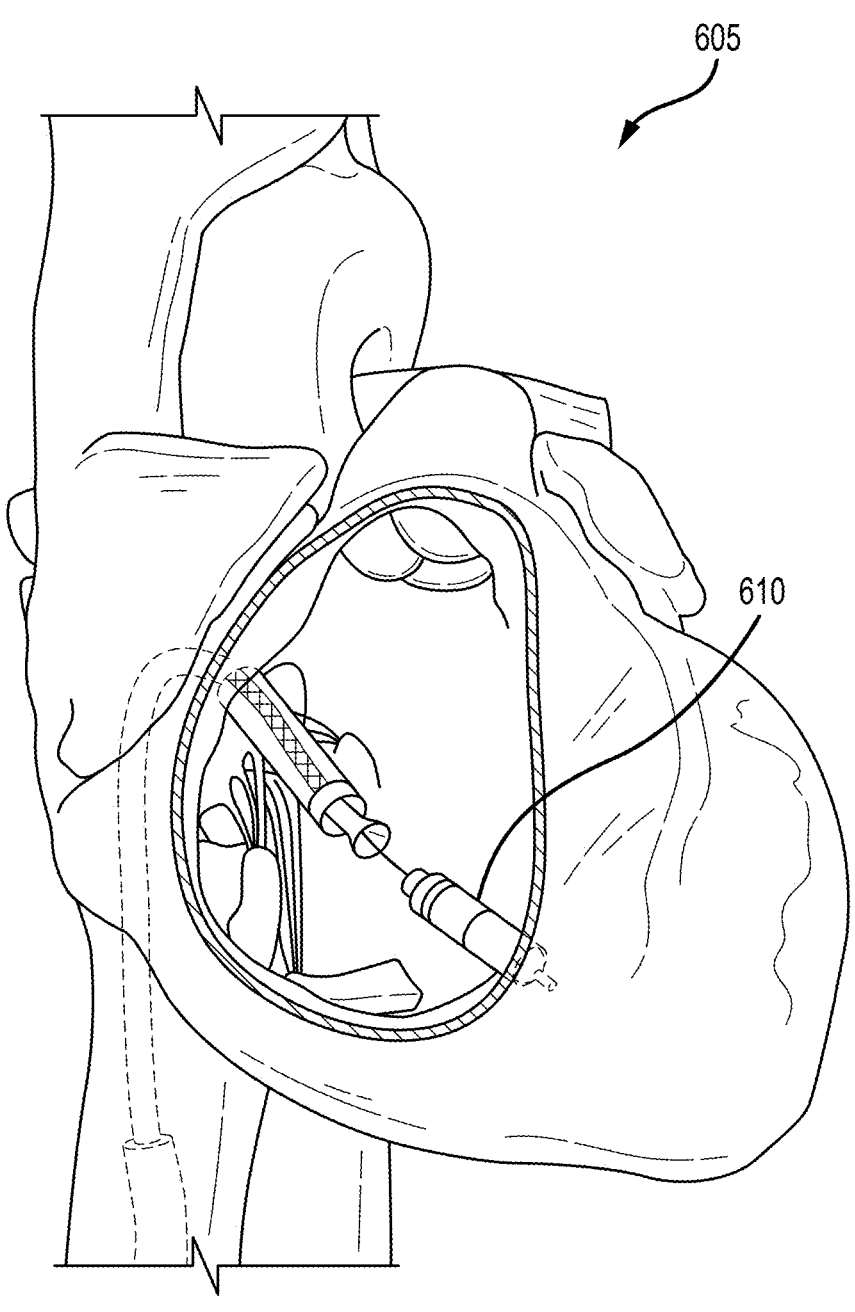

FIGS. 6A and 6B (collectively, "FIG. 6") are diagrams illustrating non-limiting examples 600 of images that may be presented as part of a display output for an IA or EI ecosystem implementation for CIED placement procedures such as leadless implant procedures or the like, in accordance with various embodiments.

Referring to the non-limiting example 600 of FIG. 6, XR displays of the heart 605 (which may be generated and presented in the manner described in detail above with respect to FIGS. 1-5, or the like) may enable a user or medical professional to more easily and accurately place leadless implants (e.g., Micra™ leadless implants, implantable cardioverter defibrillator ("ICD") devices, extravascular ICD ("EV-ICD") devices, or the like) or other implant devices in the heart or other part of the body of the patient. In some cases, the XR display may include graphical or other notations of bounds (depicted in FIG. 6A by the dark gray lines 615) and the trajectory of the device (depicted in FIG. 6A by the light gray line 620), or the like. FIG. 6B depicts the successful implantation of the device, and withdrawal of the delivery system.

Figure 7A:
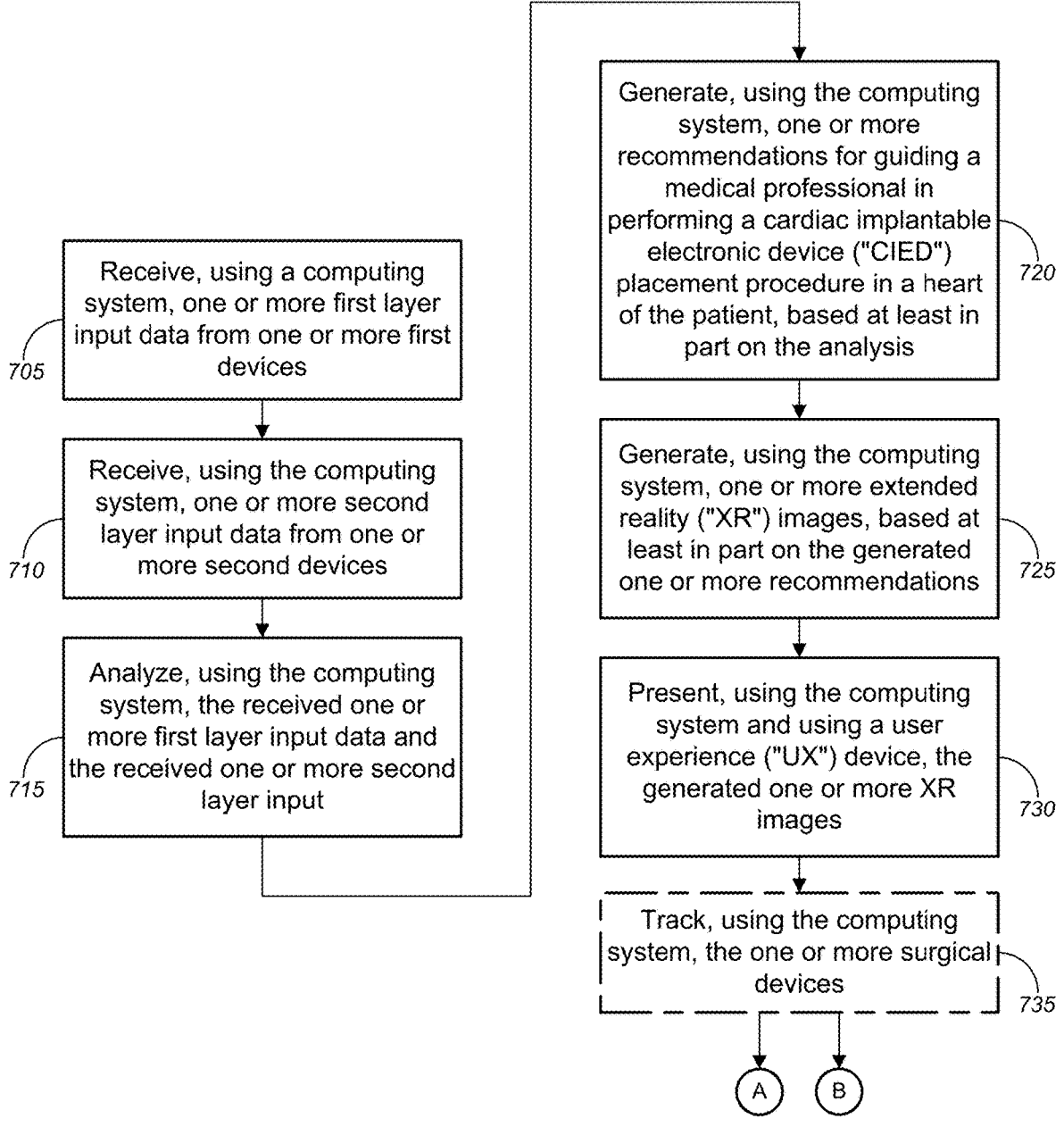

FIGS. 7A-7C (collectively, "FIG. 7") are flow diagrams illustrating a method 700 for implementing an IA or EI ecosystem for CIED placement procedures, in accordance with various embodiments. Method 700 of FIG. 7A continues onto FIG. 7B following the circular marker denoted, "A," and/or continues onto FIG. 7C following the circular marker denoted, "B."

While the techniques and procedures are depicted and/or described in a certain order for purposes of illustration, it should be appreciated that certain procedures may be reordered and/or omitted within the scope of various embodiments. Moreover, while the method 700 illustrated by FIG. 7 can be implemented by or with (and, in some cases, are described below with respect to) the systems, examples, or embodiments 100, 200, 300, 400, 500, and 600 of FIGS. 1, 2, 3, 4, 5, and 6, respectively (or components thereof), such methods may also be implemented using any suitable hardware (or software) implementation. Similarly, while each of the systems, examples, or embodiments 100, 200, 300, 400, 500, and 600 of FIGS. 1, 2, 3, 4, 5, and 6, respectively (or components thereof), can operate according to the method 700 illustrated by FIG. 7 (e.g., by executing instructions embodied on a computer readable medium), the systems, examples, or embodiments 100, 200, 300, 400, 500, and 600 of FIGS. 1, 2, 3, 4, 5, and 6 can each also operate according to other modes of operation and/or perform other suitable procedures.

In the non-limiting embodiment of FIG. 7A, method 700, at block 705, may comprise receiving, using a computing system, one or more first layer input data from one or more first devices, the one or more first layer input data comprising at least one of movement data, position data, relative distance data, or externally observable data for each of one or more persons and one or more objects within a room, and/or the like.

At block 710, method 700 may comprise receiving, using the computing system, one or more second layer input data from one or more second devices, the one or more second layer input data comprising at least one of one or more patient sensor data for monitoring procedure-relevant aspects of a patient, one or more patient imaging data for monitoring images of one or more portions of a body of the patient, or one or more navigation and mapping data for monitoring one or more surgical devices relative to the one or more portions of the body of the patient.

Method 700 may further comprise, at block 715, analyzing, using the computing system, the received one or more first layer input data and the received one or more second layer input.

Method 700 may further comprise generating, using the computing system, one or more recommendations for guiding a medical professional in performing a cardiac implantable electronic device ("CIED") placement procedure in a heart of the patient, based at least in part on the analysis, the generated one or more recommendations comprising three-dimensional ("3D") or four-dimensional ("4D") mapped guides toward, in, and around the heart of the patient (block 720); generating, using the computing system, one or more extended reality ("XR") images, based at least in part on the generated one or more recommendations (block 725); and presenting, using the computing system and using a user experience ("UX") device, the generated one or more XR images (block 730).

In some embodiments, the computing system may correspond to (or may include) the system hub or computing system 105a or 105b of system 100 of FIG. 1, or the like. According to some embodiments, the one or more devices may correspond to (or may include) the one or more devices or equipment 135 of system 100 of FIG. 1, or the like. In some instances, the one or more imaging systems may correspond to (or may include) the one or more imaging devices or systems 140 of system 100 of FIG. 1, or the like. In some cases, the one or more imaging systems may correspond to (or may include) the one or more imaging devices or systems 140 of system 100 of FIG. 1, or the like. In some instances, the UX device may correspond to (or may include) the UX devices or systems 155 of system 100 of FIG. 1 and/or the user interface aspects 295 of system 200 of FIG. 2, or the like.

According to some embodiments, method 700, at optional block 735 may comprise tracking, using the computing system, the one or more surgical devices, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

Method 700 may continue onto the process at block 740 in FIG. 7B following the circular marker denoted, "A," and/or may continue onto the process at block 760 in FIG. 7C following the circular marker denoted, "B."

At block 740 in FIG. 7B (following the circular marker denoted, "A"), method 700 may comprise receiving, using the computing system, one or more control inputs from the medical professional. Method 700 may further comprise, at block 745, analyzing, using the computing system, the received one or more control inputs in conjunction with analysis of the received one or more first layer input data and the received one or more second layer input data. Method 700, at block 750, may comprise generating, using the computing system, one or more control instructions based at least in part on the analysis, the generated one or more control instructions taking into account movement including at least one of movement of the heart and surrounding tissue due to continual beating of the heart and due to one or more of table movement, fluid loss, respiration of the patient, or movement or shifting of at least one portion of the body of the patient. Method 700 may further comprise sending, using the computing system, the generated one or more control instructions to a robotic system to cause the robotic system to implement CIED placement within the heart of the patient as part of the CIED placement procedure (block 755).

Alternatively, or additionally, at block 760 in FIG. 7C (following the circular marker denoted, "B"), method 700 may comprise receiving, using the computing system, one or more control inputs from the medical professional, including hand-movement-based control inputs resulting from movement of one or more hands of the medical professional, or the like. Method 700 may further comprise, at block 765, determining whether the hand-movement-based control inputs comprise inputs indicative of excessive movement of at least one hand of the one or more hands of the medical professional. If so, method 700, at block 770, may comprise generating, using the computing system, one or more compensated control instructions that include control instructions that are based on hand-movement-based control inputs while dampening one or more particular control inputs that are based on excessive movement of the at least one hand of the medical professional. Method 700 may further comprise sending, using the computing system, the generated one or more control instructions to a robotic system to cause the robotic system to implement CIED placement within the heart of the patient as part of the CIED placement procedure (block 775).

Exemplary System and Hardware Implementation

Figure 8:
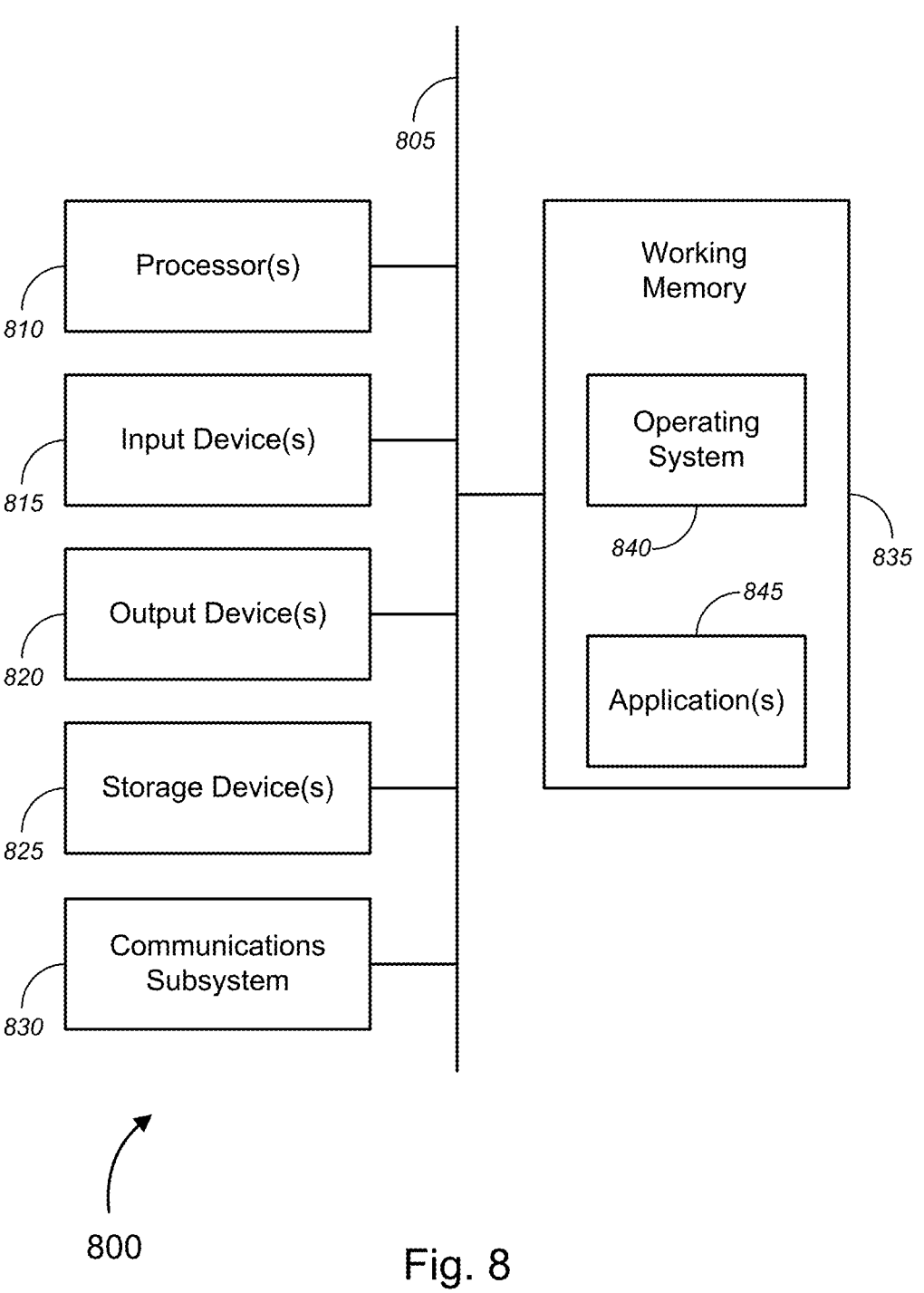
FIG. 8 is a block diagram illustrating an exemplary computer or system hardware architecture, in accordance with various embodiments.

FIG. 8 is a block diagram illustrating an exemplary computer or system hardware architecture, in accordance with various embodiments. FIG. 8 provides a schematic illustration of one embodiment of a computer system 800 of the service provider system hardware that can perform the methods provided by various other embodiments, as described herein, and/or can perform the functions of computer or hardware system (i.e., system hubs or computing systems 105a, 105b, and 205; mapping and navigation systems (e.g., electroanatomic mapping ("EAM") system, high-density mapping catheter, patient patches, navigation hardware and software, etc.) 115a, 115b, and 240; devices or equipment (e.g., robotics systems, surgical training simulator, electrosurgical generator, radiofrequency ("RF") ablation generator, cryoballoon or cryoablation catheter system, pulsed field ablation ("PFA") system, a microwave ("MW") ablation system, monitoring catheter, respiratory equipment, surgical tools, deflectable or steerable sheath, dilator, deployment device, cardiac bionic construct ("CBC"), steering subsystem, handled subsystem, pressure subsystem, coronary sinus ("CS") catheter, guidewire, introducer sheath, respiratory and other surgical equipment, transseptal needle, syringe and manifold system, etc.) 135, 135a, 135b, and 210; imaging systems (e.g., computed tomography ("CT") machine, electrophysiology ("EP") system, fluoroscopy system, etc.) 140 and 245; sensors (e.g., instrumentation, IoT sensors, biometrics system, electrogram ("EGM") or electrocardiogram ("ECG") system, camera control unit, monitor, monitoring catheter, etc.) 145 and 250; extended reality ("XR") platforms or hardware 150 and 260; user experience ("UX") devices 155 and 265; data analytics or artificial intelligence ("AI") systems 160a and 160b; anatomy or tool registration systems 165 and 220; cloud storage system 180; etc.), as described above. It should be noted that FIG. 8 is meant only to provide a generalized illustration of various components, of which one or more (or none) of each may be utilized as appropriate. FIG. 8, therefore, broadly illustrates how individual system elements may be implemented in a relatively separated or relatively more integrated manner.

The computer or hardware system 800—which might represent an embodiment of the computer or hardware system (i.e., system hubs or computing systems 105a, 105b, and 205; mapping and navigation systems 115a, 115b, and 240; devices or equipment 135, 135a, 135b, and 210; imaging systems 140 and 245; sensors 145 and 250; XR platforms or hardware 150 and 260; UX devices 155 and 265; data analytics or AI systems 160*a* and 160*b*; anatomy or tool registration systems 165 and 220; cloud storage system 180; etc.), described above with respect to FIGS. 1-7—is shown comprising hardware elements that can be electrically coupled via a bus 805 (or may otherwise be in communication, as appropriate). The hardware elements may include one or more processors 810, including, without limitation, one or more general-purpose processors and/or one or more special-purpose processors (such as micropro-cessors, digital signal processing chips, graphics accelera-tion processors, and/or the like); one or more input devices 815, which can include, without limitation, a mouse, a keyboard, and/or the like; and one or more output devices 820, which can include, without limitation, a display device, a printer, and/or the like.

The computer or hardware system 800 may further include (and/or be in communication with) one or more storage devices 825, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 800 might also include a communications subsystem 830, which can include, with-out limitation, a modem, a network card (wireless or wired), an infra-red communication device, a wireless communica-tion device and/or chipset (such as a Bluetooth™ device, an 802.11 device, a WiFi device, a WiMax device, a WWAN device, cellular communication facilities, etc.), and/or the like. The communications subsystem 830 may permit data to be exchanged with a network (such as the network described below, to name one example), with other computer or hardware systems, and/or with any other devices described herein. In many embodiments, the computer or hardware system 800 will further comprise a working memory 835, which can include a RAM or ROM device, as described above.

The computer or hardware system 800 also may comprise software elements, shown as being currently located within the working memory 835, including an operating system 840, device drivers, executable libraries, and/or other code, such as one or more application programs 845, which may comprise computer programs provided by various embodi-ments (including, without limitation, hypervisors, VMs, and the like), and/or may be designed to implement methods, and/or configure systems, provided by other embodiments, as described herein. Merely by way of example, one or more procedures described with respect to the method(s) dis-cussed above might be implemented as code and/or instruc-tions executable by a computer (and/or a processor within a computer); in an aspect, then, such code and/or instructions can be used to configure and/or adapt a general purpose computer (or other device) to perform one or more opera-tions in accordance with the described methods.

A set of these instructions and/or code might be encoded and/or stored on a non-transitory computer readable storage medium, such as the storage device(s) 825 described above. In some cases, the storage medium might be incorporated within a computer system, such as the system 800. In other embodiments, the storage medium might be separate from a computer system (i.e., a removable medium, such as a compact disc, etc.), and/or provided in an installation pack-age, such that the storage medium can be used to program, configure, and/or adapt a general purpose computer with the instructions/code stored thereon. These instructions might take the form of executable code, which is executable by the computer or hardware system 800 and/or might take the form of source and/or installable code, which, upon compi-lation and/or installation on the computer or hardware system 800 (e.g., using any of a variety of generally avail-able compilers, installation programs, compression/decom-pression utilities, etc.) then takes the form of executable code.

It will be apparent to those skilled in the art that substan-tial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable soft-ware, such as applets, etc.), or both. Further, connection to other computing devices such as network input/output devices may be employed.

As mentioned above, in one aspect, some embodiments may employ a computer or hardware system (such as the computer or hardware system 800) to perform methods in accordance with various embodiments of the invention. According to a set of embodiments, some or all of the procedures of such methods are performed by the computer or hardware system 800 in response to processor 810 executing one or more sequences of one or more instructions (which might be incorporated into the operating system 840 and/or other code, such as an application program 845) contained in the working memory 835. Such instructions may be read into the working memory 835 from another computer readable medium, such as one or more of the storage device(s) 825. Merely by way of example, execution of the sequences of instructions contained in the working memory 835 might cause the processor(s) 810 to perform one or more procedures of the methods described herein.

The terms "machine readable medium" and "computer readable medium," as used herein, refer to any medium that participates in providing data that causes a machine to operate in a specific fashion. In an embodiment imple-mented using the computer or hardware system 800, various computer readable media might be involved in providing instructions/code to processor(s) 810 for execution and/or might be used to store and/or carry such instructions/code (e.g., as signals). In many implementations, a computer readable medium is a non-transitory, physical, and/or tan-gible storage medium. In some embodiments, a computer readable medium may take many forms, including, but not limited to, non-volatile media, volatile media, or the like. Non-volatile media includes, for example, optical and/or magnetic disks, such as the storage device(s) 825. Volatile media includes, without limitation, dynamic memory, such as the working memory 835. In some alternative embodi-ments, a computer readable medium may take the form of transmission media, which includes, without limitation, coaxial cables, copper wire, and fiber optics, including the wires that comprise the bus 805, as well as the various components of the communication subsystem 830 (and/or the media by which the communications subsystem 830 provides communication with other devices). In an alterna-tive set of embodiments, transmission media can also take the form of waves (including without limitation radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 810 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 800. These signals, which might be in the form of electromagnetic signals, acoustic signals, optical signals, and/or the like, are all examples of carrier waves on which instructions can be encoded, in accordance with various embodiments of the invention.

The communications subsystem 830 (and/or components thereof) generally will receive the signals, and the bus 805 then might carry the signals (and/or the data, instructions, etc. carried by the signals) to the working memory 835, from which the processor(s) 805 retrieves and executes the instructions. The instructions received by the working memory 835 may optionally be stored on a storage device 825 either before or after execution by the processor(s) 810.

Figure 9:
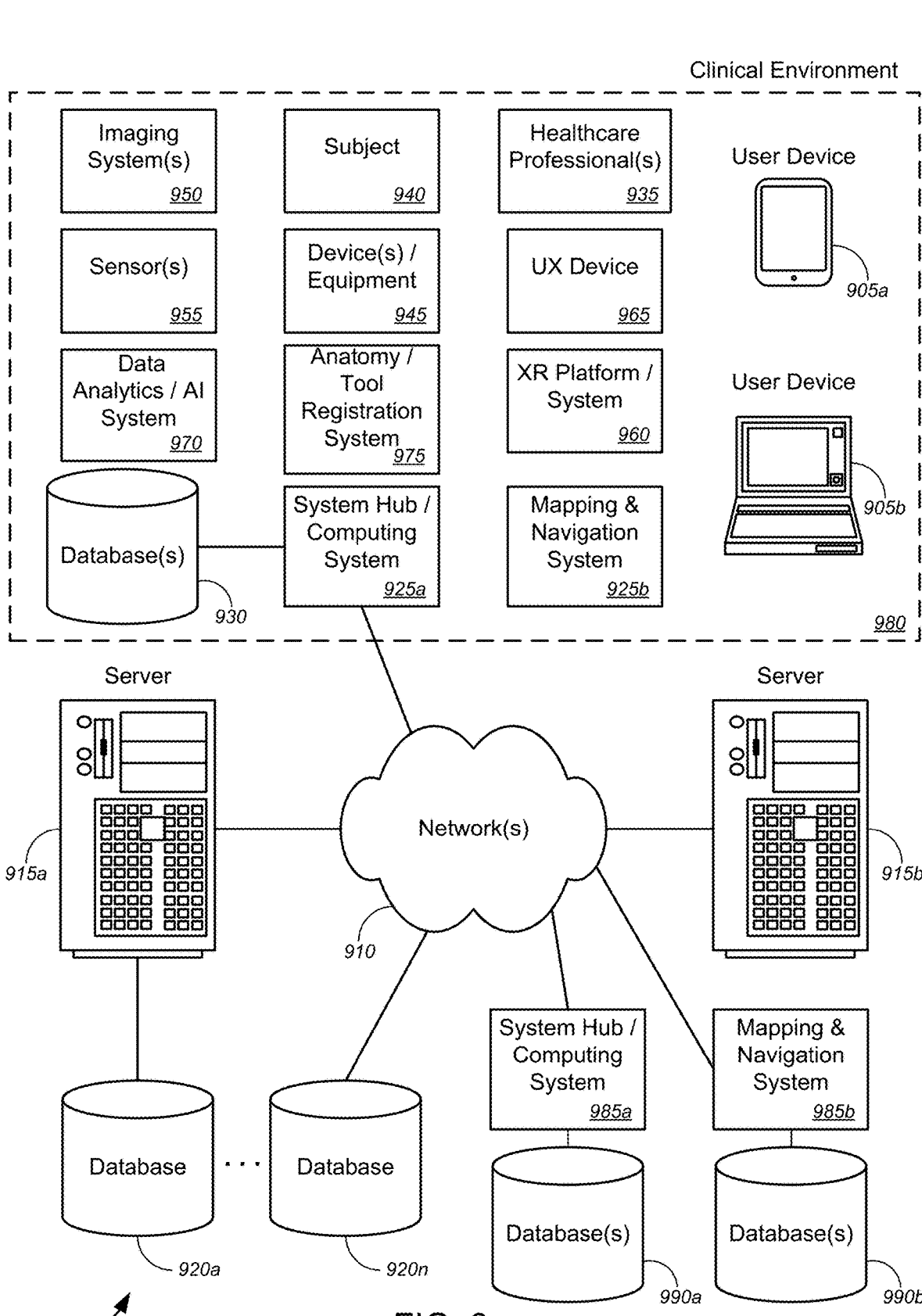
FIG. 9 is a block diagram illustrating a networked system of computers, computing systems, or system hardware architecture, which can be used in accordance with various embodiments.

As noted above, a set of embodiments comprises methods and systems for implementing medical assistance technologies, and, more particularly, to methods, systems, and apparatuses for implementing intelligent assistance ("IA") or extended intelligence ("EI") ecosystem, and even more particularly, to methods, systems, and apparatuses for implementing extended intelligence to placement procedures for cardiac implantable electronic device ("CIED") for cardiac sensing and pacing. FIG. 9 illustrates a schematic diagram of a system 900 that can be used in accordance with one set of embodiments. The system 900 can include one or more user computers, user devices, or customer devices 905. A user computer, user device, or customer device 905 can be a general purpose personal computer (including, merely by way of example, desktop computers, tablet computers, laptop computers, handheld computers, and the like, running any appropriate operating system, several of which are available from vendors such as Apple, Microsoft Corp., and the like), cloud computing devices, a server(s), and/or a workstation computer(s) running any of a variety of commercially-available UNIX™ or UNIX-like operating systems. A user computer, user device, or customer device 905 can also have any of a variety of applications, including one or more applications configured to perform methods provided by various embodiments (as described above, for example), as well as one or more office applications, database client and/or server applications, and/or web browser applications. Alternatively, a user computer, user device, or customer device 905 can be any other electronic device, such as a thin-client computer, Internet-enabled mobile telephone, and/or personal digital assistant, capable of communicating via a network (e.g., the network(s) 910 described below) and/or of displaying and navigating web pages or other types of electronic documents. Although the exemplary system 900 is shown with two user computers, user devices, or customer devices 905, any number of user computers, user devices, or customer devices can be supported.

Certain embodiments operate in a networked environment, which can include a network(s) 910. The network(s) 910 can be any type of network familiar to those skilled in the art that can support data communications using any of a variety of commercially-available (and/or free or proprietary) protocols, including, without limitation, TCP/IP, SNA™, IPX™, AppleTalk™, and the like. Merely by way of example, the network(s) 910 (similar to network(s) 175 of FIG. 1, or the like) can each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 915. Each of the server computers 915 may be configured with an operating system, including, without limitation, any of those discussed above, as well as any commercially (or freely) available server operating systems. Each of the servers 915 may also be running one or more applications, which can be configured to provide services to one or more clients 905 and/or other servers 915.

Merely by way of example, one of the servers 915 might be a data server, a web server, a cloud computing device(s), or the like, as described above. The data server might include (or be in communication with) a web server, which can be used, merely by way of example, to process requests for web pages or other electronic documents from user computers 905. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 905 to perform methods of the invention.

The server computers 915, in some embodiments, might include one or more application servers, which can be configured with one or more applications accessible by a client running on one or more of the client computers 905 and/or other servers 915. Merely by way of example, the server(s) 915 can be one or more general purpose computers capable of executing programs or scripts in response to the user computers 905 and/or other servers 915, including, without limitation, web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™, IBM™, and the like, which can process requests from clients (including, depending on the configuration, dedicated database clients, API clients, web browsers, etc.) running on a user computer, user device, or customer device 905 and/or another server 915. In some embodiments, an application server can perform one or more of the processes for implementing medical assistance technologies, and, more particularly, to methods, systems, and apparatuses for implementing IA or EI ecosystem, and even more particularly, to methods, systems, and apparatuses for implementing extended intelligence to placement procedures for cardiac implantable electronic device ("CIED") for cardiac sensing and pacing, as described in detail above. Data provided by an application server may be formatted as one or more web pages (comprising HTML, JavaScript, etc., for example) and/or may be forwarded to a user computer 905 via a web server (as described above, for example). Similarly, a web server might receive web page requests and/or input data from a user computer 905 and/or forward the web page requests and/or input data to an application server. In some cases, a web server may be integrated with an application server.

In accordance with further embodiments, one or more servers 915 can function as a file server and/or can include one or more of the files (e.g., application code, data files, etc.) necessary to implement various disclosed methods, incorporated by an application running on a user computer 905 and/or another server 915. Alternatively, as those skilled in the art will appreciate, a file server can include all necessary files, allowing such an application to be invoked remotely by a user computer, user device, or customer device 905 and/or server 915.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 920a-920n (collectively, "databases 920"). The location of each of the databases 920 is discretionary: merely by way of example, a database 920a might reside on a storage medium local to (and/or resident in) a server 915a (and/or a user computer, user device, or customer device 905). Alternatively, a database 920n can be remote from any or all of the computers 905, 915, so long as it can be in communication (e.g., via the network 910) with one or more of these. In a particular set of embodiments, a database 920 can reside in a storage-area network ("SAN") familiar to those skilled in the art. (Likewise, any necessary files for performing the functions attributed to the computers 905, 915 can be stored locally on the respective computer and/or remotely, as appropriate.) In one set of embodiments, the database 920 can be a relational database, such as an Oracle database, that is adapted to store, update, and retrieve data in response to SQL-formatted commands. The database might be controlled and/or maintained by a database server, as described above, for example.

According to some embodiments, system 900 might further comprise system hub or computing system 925a and corresponding database(s) 930 (similar to system hub or computing system 105a and 205, and corresponding database(s) 110a of FIGS. 1 and 2, or the like), mapping and navigation system 925b (similar to mapping and navigation system 115a and 240 of FIGS. 1 and 2, or the like), one or more healthcare professionals 935 (similar to healthcare professional(s) 125 of FIG. 1, or the like), a subject 940 (similar to subjects 130 and 230 of FIGS. 1 and 2, or the like), one or more devices or equipment 945 (similar to devices or equipment 135, 135a, 135b, and 210 of FIGS. 1 and 2, or the like), one or more imaging systems 950 (similar to imaging system(s) 140 of FIG. 1, or the like), one or more sensors 955 (similar to sensors 145 and 245 of FIGS. 1 and 2, or the like), an extended reality ("XR") platform or system 960 (similar to XR platform or systems 150 and 260 of FIGS. 1 and 2, or the like), a user experience ("UX") device 965 (similar to UX devices 155 and 265 of FIGS. 1 and 2, or the like), a data analytics or artificial intelligence ("AI") system 970 (similar to data analytics or AI system 160a of FIG. 1, or the like), and/or an anatomy or tool registration system 975 (similar to anatomy or tool registration systems 165 and 220 of FIGS. 1 and 2, or the like), and/or the like. In some instances, the system hub or computing system 925a and corresponding database(s) 930, the mapping and navigation system 925b, the one or more healthcare professional(s) 935, the subject 940, the one or more devices or equipment 945, the one or more imaging systems 950, the one or more sensors 955, the XR platform or system 960, the UX device 965, the data analytics or AI system 970, or the anatomy or tool registration system 975, and/or the like, together with the user devices 905a and 905b may be located or disposed within clinical environment 980. In some cases, the clinical environment 980 might include, but is not limited to, a clinic, a hospital, an operating room, an emergency room, a physician's office, or a laboratory, or the like.

In some embodiments, the system 900 might further comprise remote system hub or computing system 985a and corresponding database(s) 990a (similar to system hub or computing system 105b and corresponding database(s) 110b of FIG. 1, or the like), and remote mapping and navigation system 985b and corresponding database(s) 990b (similar to mapping and navigation system 115b and corresponding database(s) 120b of FIG. 1, or the like), or the like, that communicatively couple to the system hub or computing system 925a via network(s) 910.

In operation, system hub or computing system 925a or 985a (collectively, "computing system" or the like) might receive one or more first layer input data from one or more first devices, the one or more first layer input data comprising at least one of movement data, position data, relative distance data, or externally observable data for each of one or more persons (e.g., subject 940, healthcare professional(s) 935, etc.) and one or more objects (e.g., device(s) or equipment 945, furniture, etc.) within a room (i.e., clinical environment 980, or the like). In such cases, the one or more first devices may include at least one of imaging system(s) 950, sensor(s) 955, and/or the like, that are configured to obtain, capture, or otherwise provide the one or more first layer input data. The computing system might receive one or more second layer input data from one or more second devices, the one or more second layer input data comprising at least one of one or more patient sensor data for monitoring procedure-relevant aspects of a patient (i.e., subject 940), one or more patient imaging data for monitoring images of one or more portions of a body of the patient, or one or more navigation and mapping data for monitoring one or more surgical devices (i.e., the devices or equipment 945, or the like) relative to the one or more portions of the body of the patient, and/or the like. In such cases, the one or more second devices may include at least one of device(s) or equipment 945, imaging system(s) 950, sensor(s) 955, and/or the like, that are configured to obtain, capture, or otherwise provide the one or more second layer input data.

The computing system might analyze the received one or more first layer input data and the received one or more second layer input. The computing system might generate one or more recommendations for guiding a medical professional (i.e., healthcare professional(s) 935, or the like) in performing a cardiac implantable electronic device ("CIED") placement procedure in a heart of the patient, based at least in part on the analysis, the generated one or more recommendations comprising 3D or 4D mapped guides toward, in, and around the heart of the patient. The computing system might then generate one or more XR images (or one or more XR experiences), based at least in part on the generated one or more recommendations, and might present the generated one or more XR images (or one or more XR experiences) using a UX device 965. According to some embodiments, the one or more XR images might be dynamic images, which might include an overlay of data models depicting at least one of electrical pulses, blood flow, tissue movement, damage, stress, and/or the like, and thus may not be a still frame in 3D. In some embodiments, the one or more XR images might include, without limitation, at least one of one or more AR images, one or more AR videos, one or more VR images, one or more VR videos, one or more MR images, one or more MR videos, one or more XR images, or one or more XR videos, and/or the like.

According to some embodiments, the generated one or more XR images might be presented to provide one or more of: a guide for a medical professional (e.g., healthcare professional(s) 935, or the like), a navigation tool during the CIED placement procedure, a proximity detection tool during the CIED placement procedure, a 3D or 4D visualization view of the at least one or more portions of the patient, a heads-up display of at least one of the one or more first layer input data, a heads-up display of at least one of the one or more patient sensor data, a heads-up display of at least one of the one or more patient imaging data, a heads-up display of physiological data of the patient, or a heads-up display of procedure-related data of the patient, and/or the like. In some instances, generating the one or more XR images might comprise combining or mapping the received one or more first layer input data and the received one or more second layer input into a combined 3D or 4D representation, based at least in part on the analysis and the generated one or more recommendations; and generating the one or more XR images based on the combined 3D or 4D representation.

In some embodiments, the computing system might track the one or more surgical devices (e.g., devices or equipment 945, or the like), using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system, and/or the like.

According to some embodiments, the computing system might receive one or more control inputs from the medical professional; might analyze the received one or more control inputs in conjunction with analysis of the received one or more first layer input data and the received one or more second layer input data; might generate one or more control instructions based at least in part on the analysis, the generated one or more control instructions taking into account movement including at least one of movement of the heart and surrounding tissue due to continual beating of the heart and due to one or more of table movement, fluid loss, respiration of the patient, or movement or shifting of at least one portion of the body of the patient; and might send the generated one or more control instructions to a robotic system (which may, in some cases, be included among the device(s) or equipment 945, or the like) to cause the robotic system to implement CIED placement within the heart of the patient as part of the CIED placement procedure.

In some instances, at least the processes of receiving the one or more first layer input data, the one or more second layer input data, analyzing the received one or more first layer input data and the received one or more second layer input, generating the one or more recommendations, generating the one or more XR images, presenting the generated one or more XR images, receiving the one or more control inputs, analyzing the received one or more control inputs, generating the one or more control instructions, and/or sending the generated one or more control instructions may occur in a manner that is at least one of continual, dynamic, feedback-looped, updated, in real-time, or in near-real-time, and/or the like, during the course of the CIED placement procedure. According to some embodiments, real-time display of simulations and interactions in XR for one or more of statistical shape modeling ("SSM") of anatomy, finite element analysis ("FEA"), electrical wave propagation, computation fluid dynamics, and/or the like (collectively, "analytical tools" or the like), may be coupled with XR and AI to aid in the placement of a heart valve where flow could be predicted (or, in the case of a lead or ablation, where the wave propagation could be simulated) and displayed before the final placement, or the like.

In some embodiments, the received one or more control inputs may comprise hand-movement-based control inputs resulting from movement of one or more hands of the medical professional. In such cases, analyzing the received one or more control inputs may comprise determining whether the hand-movement-based control inputs comprise inputs indicative of excessive movement of at least one hand of the one or more hands of the medical professional. As such, generating the one or more control instructions may comprise, based on a determination that the hand-movement-based control inputs comprise inputs indicative of excessive movement of at least one hand of the medical professional, the computing system generating one or more compensated control instructions that include control instructions that are based on hand-movement-based control inputs while dampening one or more particular control inputs that are based on excessive movement of the at least one hand of the medical professional.

These and other functions of the system 900 (and its components) are described in greater detail above with respect to FIGS. 1-7.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

COPYRIGHT STATEMENT

What is claimed is:

1. A method, comprising:

receiving, using a computing system and during a cardiac implantable electronic device ("CIED") placement procedure for a patient, one or more first layer input data from one or more first devices, the one or more first layer input data comprising at least one of movement data, position data, relative distance data, or externally observable data, wherein the at least one of movement data, position data, relative distance data, or externally observable data pertains to each of one or more persons and one or more objects within a real-world clinical environment for performing the CIED placement procedure, wherein the one or more persons include medical staff other than a medical professional performing the CIED placement procedure;

receiving, using the computing system, one or more second layer input data from one or more second devices, the one or more second layer input data comprising at least one of one or more patient sensor data for monitoring procedure-relevant aspects of the patient, one or more patient imaging data for monitoring images of one or more portions of a body of the patient, or one or more navigation and mapping data for monitoring one or more surgical devices relative to the one or more portions of the body of the patient;

analyzing, using the computing system, the received one or more first layer input data and the received one or more second layer input data;

generating, using the computing system, one or more recommendations for guiding the medical professional in performing the CIED placement procedure in a heart of the patient, based at least in part on the analysis, the generated one or more recommendations comprising three-dimensional ("3D") or four-dimensional ("4D") mapped guides toward, in, or around the heart of the patient, the 3D or 4D mapped guides comprising one or more graphical bounds for the CIED or a trajectory of the CIED to guide the medical professional in performing the CIED placement procedure;

generating, using the computing system, one or more extended reality ("XR") images, based at least in part on the generated one or more recommendations;

presenting, using the computing system and using a user experience ("UX") device, the generated one or more XR images; and generating, using the computing system, one or more control instructions to at least one robotic system based at least in part on the analysis of the received one or more first layer input data and the received one or more second layer input data.

2. The method of claim 1, wherein the computing system comprises at least one of an XR computing system, a medical procedure computing system, a hub computing system, a 3D graphical processing unit, a cluster computing system, a 4D graphics computing system, a server computer, a cloud computing system, or a distributed computing system.

3. The method of claim 1, wherein the one or more surgical devices comprise at least one of one or more catheters, one or more catheter interconnect cables, one or more leads, one or more pacemakers, one or more defibrillators, one or more rigid robotic devices, one or more soft robotic devices, one or more robotic systems, one or more robotic arms, one or more needles, one or more therapeutic delivery devices, one or more implant delivery devices, one or more diagnostic devices, one or more diagnostic catheters, one or more implant devices, one or more surgical tools, one or more monitoring devices, one or more cameras, one or more imaging tools, one or more fiducials, one or more staples, one or more anchors, one or more embolic protection devices, one or more cardiomyoplasty tools, one or more vascular closure tools, one or more septal closure tools, one or more guide wires, one or more introducers, one or more sheaths, an implantable cardioverter defibrillator ("ICD") device, an extravascular ICD ("EV-ICD"), a miniature leadless implant, a conduction system pacing ("CSP") device, an implantable bradycardia pacemaker with leads, a leadless bradycardia pacemaker, a low power implantable cardiac resynchronization therapy ("CRT-P") device, a high power implantable cardiac resynchronization therapy ("CRT-D") device, or one or more capital equipment.

4. The method of claim 1, wherein the one or more patient sensor data are obtained using one or more sensors comprising at least one of one or more chronically implanted sensors, one or more diagnostic sensors, one or more surgical sensors, one or more wearable sensors, one or more gas sensors, one or more optical sensors, one or more impedance sensors, one or more ultrasound sensors, one or more flow sensors, one or more blood velocity sensors, one or more blood volume sensors, one or more electrical sensors, one or more voltage sensors, one or more amperage sensors, one or more wattage sensors, one or more impedance sensors, one or more motion sensors, one or more sound sensors, one or more blood pressure sensors, one or more heart rate sensors, one or more pulse sensors, one or more oxygen sensors, one or more carbon dioxide ("$CO_2$") sensors, one or more fluid levels, one or more doppler sensors, one or more biomarker sensors, one or more perfusion sensors, one or more electromyography ("EMG") sensors, one or more sleep sensors, one or more cardiac hemodynamics sensors, one or more ischemia sensors, one or more hematocrit ("HCT") level sensors, one or more biometric sensors, one or more electroencephalographic ("EEG") sensors, or one or more pain sensors.

5. The method of claim 1, wherein the one or more patient imaging data are obtained using one or more imaging devices comprising at least one of a magnetic resonance imaging ("MRI") system, a computed tomography ("CT") system, an ultrasound ("US") system, an electromechanical wave imaging ("EWI") system, a magnetic resonance angiography ("MRA") system, a computed tomography angiography ("CTA") system, a blood oxygen-level dependent signal ("BOLD") system, an electroencephalography ("EEG") system, an optical coherence tomography ("OCT") system, a dynamic susceptibility contrast ("DSC") MRI system, a fluoroscopy system, an X-ray system, or an endoscopy system.

6. The method of claim 1, wherein the CIED placement procedure comprises at least one of a cardiac mapping procedure, a cardiac resynchronization therapy ("CRT") device installation procedure, a right ventricular pacing ("RVP") procedure, a His bundle pacing ("HBP") procedure, a left bundle branch pacing ("LBBP") lead placement procedure, a right bundle branch pacing ("RBBP") lead placement procedure, a bilateral bundle branch area pacing ("BBBP") lead placement procedure, an implant procedure, an implantable cardioverter defibrillator ("ICD") device installation procedure, an extravascular ICD ("EV-ICD") device installation procedure, a pacemaker installation procedure, a miniature leadless implant installation procedure, or a remote monitoring device installation procedure.

7. The method of claim 1, wherein the one or more XR images comprise at least one of one or more augmented reality ("AR") images, one or more AR videos, one or more virtual reality ("VR") images, one or more VR videos, one or more mixed reality ("MR") images, one or more MR videos, one or more XR images, or one or more XR videos.

8. The method of claim 1, wherein the UX device comprises at least one of a headset, UX glasses, a viewing window, a supplement to existing glasses, headphones, UX contact lenses, a heads-up display ("HUD") device, a 3D spatial sound system, a telemonitoring system, a rigid robotic device control and sensory feedback system, a soft robotic device control and sensory feedback system, an eye control system, a voice control system, a remote control system, a gesture-based control system, a sign language-based control system, a body-part-based control system, a joystick, a mouse, a two-dimensional ("2D") screen display, a 3D refractive display, a parallel reality system, a projection system, a 3D printed reconstruction system, a customized view generation system, a ghosting and prediction system, a master-slave control system, an annotation system, or a haptic feedback system.

9. The method of claim 1, wherein the generated one or more XR images are presented to provide one or more of: a guide for the medical professional, a navigation tool during the CIED placement procedure, a proximity detection tool during the CIED placement procedure, a 3D or 4D visualization view of the at least one or more portions of the patient, a heads-up display of at least one of the one or more first layer input data, a heads-up display of at least one of the one or more patient sensor data, a heads-up display of at least one of the one or more patient imaging data, a heads-up display of physiological data of the patient, or a heads-up display of procedure-related data of the patient.

10. The method of claim 1, further comprising:

tracking, using the computing system, the one or more surgical devices, using at least one of an electropotential-based tracking system, an impedance-based tracking system, an electromagnetic-based tracking system, a magnetic anomaly detection-based tracking system, a radio frequency identification ("RFID")-based tracking system, a Bluetooth-based tracking system, a wireless-based tracking system, an optical-based tracking system, a laser-based tracking system, an ultrasound ("US") imaging-based tracking system, a computer vision-based tracking system, a fluoroscopy-based tracking system, an MRI-based tracking system, an accelerometer-based tracking system, a global positioning system ("GPS")-based tracking system, an infrared ("IR")-based tracking system, an ultrasonic sound-based tracking system, a piezoelectric-based tracking system, a simultaneous localization and mapping ("SLAM")-based tracking system, an acoustic-based tracking system, a radar-based tracking system, a feature identification-based tracking system, a machine learning-based tracking system, a predictive tracking system, a prescriptive tracking system, or a near-field communications-based tracking system.

11. The method of claim 1, wherein generating, using the computing system, one or more control instructions to at least one robotic system based at least in part on the analysis of the received one or more first layer input data and the received one or more second layer input data further comprises:

receiving, using the computing system, one or more control inputs from the medical professional;

analyzing, using the computing system, the received one or more control inputs in conjunction with the analysis of the received one or more first layer input data and the received one or more second layer input data;

generating, using the computing system, the one or more control instructions based at least in part on the analysis of the received one or more control inputs in conjunction with the analysis of the received one or more first layer input data and the received one or more second layer input data, the generated one or more control instructions taking into account movement including at least one of movement of the heart and surrounding tissue due to continual beating of the heart and due to one or more of table movement, fluid loss, respiration of the patient, or movement or shifting of at least one portion of the body of the patient; and sending, using the computing system, the generated one or more control instructions to the at least one robotic system to cause the at least one robotic system to implement CIED placement within the heart of the patient as part of the CIED placement procedure.

12. The method of claim 11, wherein at least the processes of receiving the one or more first layer input data, the one or more second layer input data, analyzing the received one or more first layer input data and the received one or more second layer input, generating the one or more recommendations, generating the one or more XR images, presenting the generated one or more XR images, receiving the one or more control inputs, analyzing the received one or more control inputs, generating the one or more control instructions, and sending the generated one or more control instructions occur in a manner that is at least one of continual, dynamic, feedback-looped, updated, in real-time, or in near-real-time during the course of the CIED placement procedure.

13. The method of claim 11, wherein the received one or more control inputs comprise hand-movement-based control inputs resulting from movement of one or more hands of the medical professional, wherein analyzing the received one or more control inputs comprises determining whether the hand-movement-based control inputs comprise inputs indicative of excessive movement of at least one hand of the one or more hands of the medical professional, and wherein generating the one or more control instructions comprises, based on a determination that the hand-movement-based control inputs comprise inputs indicative of excessive movement of at least one hand of the medical professional, generating, using the computing system, one or more compensated control instructions that include control instructions that are based on hand-movement-based control inputs while dampening one or more particular control inputs that are based on excessive movement of the at least one hand of the medical professional.

14. The method of claim 1, wherein the method is performed without use of fluoroscopy.

15. The method of claim 1, wherein the generated one or more recommendations comprise 3D or 4D mapped guides toward, in, and around the heart of the patient.

16. An apparatus, comprising:
    at least one processor; and
    a non-transitory computer readable medium communicatively coupled to the at least one processor, the non-transitory computer readable medium having stored thereon computer software comprising a set of instructions that, when executed by the at least one processor, causes the apparatus to:
        receive, during a cardiac implantable electronic device ("CIED") placement procedure for a patient, one or more first layer input data from one or more first devices, the one or more first layer input data comprising at least one of movement data, position data, relative distance data, or externally observable data, wherein the at least one of movement data, position data, relative distance data, or externally observable data pertains to each of one or more persons and one or more objects within a real-world clinical environment for performing the CIED placement procedure, wherein the one or more persons include medical staff other than a medical professional performing the CIED placement procedure;
        receive one or more second layer input data from one or more second devices, the one or more second layer input data comprising at least one of one or more patient sensor data for monitoring procedure-relevant aspects of the patient, one or more patient imaging data for monitoring images of one or more portions of a body of the patient, or one or more navigation and mapping data for monitoring one or more surgical devices relative to the one or more portions of the body of the patient;
        analyze the received one or more first layer input data and the received one or more second layer input data;

generate one or more recommendations for guiding the medical professional in performing the CIED placement procedure in a heart of the patient, based at least in part on the analysis, the generated one or more recommendations comprising three-dimensional ("3D") or four-dimensional ("4D") mapped guides toward, in, or around the heart of the patient, the 3D or 4D mapped guides comprising one or more graphical bounds for the CIED or a trajectory of the CIED to guide the medical professional in performing the CIED placement procedure;
        generate one or more extended reality ("XR") images, based at least in part on the generated one or more recommendations;
        present, using a user experience ("UX") device, the generated one or more XR images; and
        generate one or more control instructions to at least one robotic system based at least in part on the analysis of the received one or more first layer input data and the received one or more second layer input data.

17. The apparatus of claim 16, wherein the generated one or more recommendations comprise 3D or 4D mapped guides toward, in, and around the heart of the patient.

18. A system, comprising:
    a computing system, comprising:
        at least one first processor; and
        a first non-transitory computer readable medium communicatively coupled to the at least one first processor, the first non-transitory computer readable medium having stored thereon computer software comprising a first set of instructions that, when executed by the at least one first processor, causes the computing system to:
            receive, during a cardiac implantable electronic device ("CIED") placement procedure for a patient, one or more first layer input data from one or more first devices, the one or more first layer input data comprising at least one of movement data, position data, relative distance data, or externally observable data, wherein the at least one of movement data, position data, relative distance data, or externally observable data pertains to each of one or more persons and one or more objects within a real-world clinical environment for performing the CIED placement procedure, wherein the one or more persons include medical staff other than a medical professional performing the CIED placement procedure;
            receive one or more second layer input data from one or more second devices, the one or more second layer input data comprising at least one of one or more patient sensor data for monitoring procedure-relevant aspects of the patient, one or more patient imaging data for monitoring images of one or more portions of a body of the patient, or one or more navigation and mapping data for monitoring one or more surgical devices relative to the one or more portions of the body of the patient;
            analyze the received one or more first layer input data and the received one or more second layer input data;
            generate one or more recommendations for guiding the medical professional in performing the CIED placement procedure in a heart of the patient, based at least in part on the analysis, the generated one or more recommendations comprising three-dimensional ("3D") or four-dimensional ("4D")

mapped guides toward, in, or around the heart of the patient, the 3D or 4D mapped guides comprising one or more graphical bounds for the CIED or a trajectory of the CIED to guide the medical professional in performing the CIED placement procedure;

generate one or more extended reality ("XR") images, based at least in part on the generated one or more recommendations;

present, using a user experience ("UX") device, the generated one or more XR images; and generate one or more control instructions to at least one robotic system based at least in part on the analysis of the received one or more first layer input data and the received one or more second layer input data.

19. The system of claim 18, wherein the generated one or more recommendations comprise 3D or 4D mapped guides toward, in, and around the heart of the patient.

*  *  *  *  *